United States Patent [19]

Yoshino et al.

[11] Patent Number: 4,707,468

[45] Date of Patent: Nov. 17, 1987

[54] POLYPEPTIDE

[75] Inventors: Hiroshi Yoshino, Abiko; Yutaka Tsuchiya, Ushikumachi; Takeru Kaneko, Yatabe; Takahiro Nakazawa, Fujishiro, all of Japan; Masuhiro Ikeda, Miami Springs, Fla.; Shin Araki, Yatabemachi, Japan; Kiyomi Yamatsu, Kamakura, Japan; Shinro Tachibana, Kashiwa, Japan; Yoshihiro Arakawa, Ibaraki, Japan

[73] Assignee: Eisai Co., Ltd., Tokyo, Japan

[21] Appl. No.: 796,390

[22] Filed: Nov. 8, 1985

[30] Foreign Application Priority Data

Nov. 9, 1984 [JP] Japan ................. 59-236076

[51] Int. Cl.$^4$ .................. H61K 37/02; C07K 7/12; C07K 7/06

[52] U.S. Cl. ..................... 514/16; 514/809; 530/302; 530/328; 530/329

[58] Field of Search ............... 530/302; 514/16, 809; 530/328, 329

[56] References Cited

U.S. PATENT DOCUMENTS

| | | | |
|---|---|---|---|
| 4,127,533 | 11/1978 | Coy et al. | 530/302 |
| 4,139,504 | 2/1979 | Coy et al. | 530/302 |
| 4,148,786 | 4/1979 | Sakantakis | 530/302 |
| 4,178,284 | 12/1979 | Sarantakis | 530/302 |
| 4,254,106 | 3/1981 | Wilkinson | 530/302 |
| 4,343,795 | 8/1982 | Wilkinson | 530/302 |
| 4,346,083 | 8/1982 | Wilkinson | 530/302 |
| 4,371,463 | 2/1983 | Pert et al. | 530/302 |
| 4,518,711 | 5/1985 | Hruby et al. | 530/302 |
| 4,555,403 | 11/1985 | Brantl et al. | 530/302 |

Primary Examiner—Delbert R. Phillips
Attorney, Agent, or Firm—Flynn, Thiel, Boutell & Tanis

[57] ABSTRACT

A novel polypeptide is defined by the below shown formula and is useful as an analgesic.

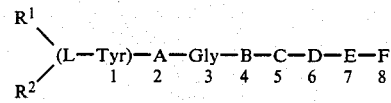

wherein $R^1$ and $R^2$ may be the same or different and each represents a hydrogen atom or a lower alkyl or lower alkenyl group, A represents a D-amino acid, Gly or Sar provided that when the D-amino acid is D-Cys, it is bonded with L-Cys or D-Cys in position 5 through a S—S bond to effect intramolecular ring closure, B represents L-Phe or D-Phe in which the benzene ring may be substituted or an α-N-alkyl derivative thereof, C represents an L-amino acid, D-Cys or an α-N-alkyl derivative thereof, D and E each represent an L- or D-basic amino acid or an α-N-alkyl derivative thereof, F represents a group of the formula —OR$^3$ (in which R$^3$ is H or a lower alkyl group), a group of the formula:

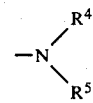

(in which $R^4$ and $R^5$ are the same or different and each represents H or a lower alkyl group), a group of the formula: —G—OR$^6$ (in which G is an L- or D-amino acid or Gly or an α-N-alkyl derivative thereof and R$^6$ represents H or a lower alkyl group), a group of the formula:

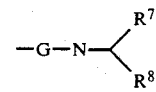

(in which G is as defined above and $R^7$ and $R^8$ may be the same or different and each represents H or a lower alkyl group), a group of the formula: —G—L—Arg—OR$^9$ or —G—D—Arg—OR$^9$ (in which G is as defined above and $R^9$ represents H or a lower alkyl group or a group of the formula:

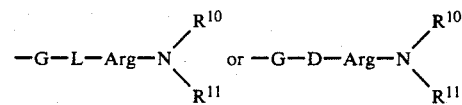

(in which G is as defined above and $R^{10}$ and $R^{11}$ may be the same or different and each represents H or a lower alkyl group), a group of the formula: —G—J—OR$^{12}$ in which G is defined as above, J is a neutral amono acid group or an acidic amino acid group and $R^{12}$ is hydrogen or a lower alkyl group; or a group of the formula: —G—Arg—M—OR$^{13}$ in which M is D-amino acid group and $R^{13}$ is hydrogen or a lower alkyl group, provided that all of the amino acids constituting the polypeptide of the above formula do not represent at the same time an L-amino acid of the general formula:

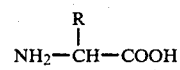

(in which R represents a group corresponding to a structural formula of an amino acid deprived of a group of the formula:

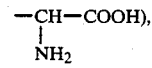

or pharmacologically acceptable salts of them.

29 Claims, No Drawings

POLYPEPTIDE

The present invention relates to polypeptides having excellent medicinal effects. More particularly, the invention relates to polypeptides of the following general formula (I):

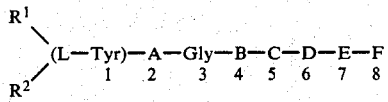

wherein $R^1$ and $R^2$ can be the same or different and each represents a hydrogen atom or a lower alkyl or lower alkenyl group; A represents a D-amino acid, Gly or Sar, provided that when the D-amino acid is D-Cys, it is bonded with L-Cys or D-CYs located in position 5 through a S-S bond to effect intramolecular ring closure; B represents L-Phe or D-Phe in which the benzene ring may be substituted or an α-N-alkyl derivative thereof; C represents an L-amino acid, D-Cys or an α-N-alkyl derivative thereof, with the proviso that when A is D-Cys, C is L-Cys or D-Cys and is bonded with A through a S—S bond as described above; D and E each represent an L- or D-basic amino acid or an α-N-alkyl derivative thereof; F represents a group of the formula: —$OR^3$ (in which $R^3$ is H or a lower alkyl group) a group of the formula:

(in which $R^4$ and $R^5$ are the same or different and each represents H or a lower alkyl group), a group of the formula: -G-$OR^6$ (in which G is an L- or D-amino acid or Gly or an α-N-alkyl derivative thereof and $R^6$ represents H or a lower alkyl group), a group of the formula:

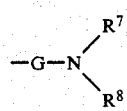

(in which G is the same as defined above and $R^7$ and $R^8$ may be the same or different and each represents H or a lower alkyl group), a group of the formula: -G-(L-Arg)-$OR^9$ or -G-(D-Arg)-$OR^9$ (in which G is the same as defined above and $R^9$ represents H or a lower alkyl group), a group of the formula:

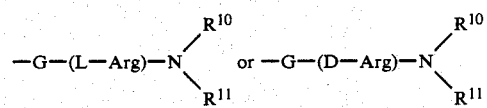

(in which G is the same as defined above and $R^{10}$ and $R^{11}$ can be the same or different and each represents H or a lower alkyl group), a group of the formula: -G-J-$OR^{12}$ in which G is the same as defined as above, J is a neutral amino acid group or an acidic amino acid group and $R^{12}$ is hydrogen or a lower alkyl group; or a group of the formula: -G-Arg-M-$OR^{13}$ in which M is a D-amino acid group and $R^{13}$ is hydrogen or a lower alkyl group, provided that all of the amino acids constituting any one given polypeptide of the above formula do not simultaneously represent an L-amino acid of the general formula:

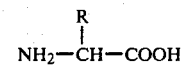

(in which R represents a group corresponding to a structural formula of an amino acid deprived of a group of the formula:

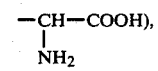

that is, at least one of the amino acids of a given polypeptide must be a D-amino acid or an α-N-alkyl derivative of a D- or L-amino acid, or pharmacologically acceptable salts of them, as well as a process for producing them and medicines containing them.

The amino acids constituting the peptides herein include D- and L-amino acids. Unless otherwise stated, the amino acids are L-amino acids. The symbols used herein have the same meanings as is the general practice in the field of peptide chemistry. Namely, they are as follows:

| | |
|---|---|
| Tyr: | tyrosine |
| Gly: | glycine |
| Sar: | sarcosine |
| Cys: | cysteine |
| Phe: | phenylalanine |
| Arg: | arginine |
| Leu: | leucine |
| Ile: | isoleucine |
| Nle: | norleucine |
| Met: | methionine |
| Met(O): | methionine sulfoxide |
| Ser: | serine |
| Val: | valine |
| homo-Arg: | homoarginine |
| Orn: | ornithine |
| Glu: | glutamic acid |
| Trp: | tryptophan |
| Asp: | aspartic acid |
| Ala: | alanine |
| Pro: | proline |
| Gln: | glutamine |
| Asn: | Asparaginine |
| Aib: | 2-aminoisobutyric acid |
| Phe(p-Cl): | p-chlorophenylalanine |
| Phe(p-Br): | p-bromophenylalanine |
| Phe(p-NO$_2$): | p-nitrophenylalanine |
| Phe(p-I): | p-iodophenylalanine |
| Phe(p-F): | p-fluorophenylalanine |
| Phe(p-CH$_3$): | p-methylphenylalanine |
| Phe(p-CH$_3$O): | p-methoxyphenylalanine |
| Phe(p-CF$_3$): | p-trifluoromethylphenylalanine |
| BOC: | tert-butoxycarbonyl |
| Z: | benzyloxycarbonyl |
| Cl$_2$Bzl: | 2,6-dichlorobenzyl |
| CH$_3$Bzl: | 4-methylbenzyl |
| Tos: | p-toluenesulfonyl, and |
| Bzl: | benzyl |

PRIOR ART

The findings obtained in investigations of the mechanism of analgesic effects of morphine suggest that the living body contains so-called endogenous morphine-like substances which control various vital sensations, such as those of pain and mental action. After a series of studies, enkephalin and endorphin were isolated as opioid peptides and the structures of them were determined. Thereafter, intensive investigations were made further in this art and various new opioid peptides such as β-neoendorphin, β-casomorphin, kyotorphin, dermorphin and dynorphin were found.

Among them, dynorphin is an opioid peptide of the following structural formula found by some of the inventors of the present invention:

H-Tyr-Gly-Gly-Phe-Leu-Arg-Arg-Ile-Arg-Pro-Lys-Leu-Lys-Trp-Asp-Asn-Gln-OH

Dynorphin is a natural opioid peptide having specific effects on a K-receptor and, therefore, the use of it as an analgesic having no side effects, such as tolerance or dependency, is expected.

PROBLEMS TO BE SOLVED BY THE INVENTION

However, dynorphin has the defect that it cannot exhibit an analgesic effect, as such, when it is administered by intravenous injection, because it is unstable in the blood.

Further, a highly active peptide having a shorter chain is demanded, since dynorphin is a heptadecapeptide having a relatively long chain.

DISCLOSURE OF THE INVENTION

The inventors have made intensive investigations of peptides having chains shorter than that of dynorphin and capable of exhibiting an analgesic effect, when administered by both intravenous and subcutaneous injection, and finally have discovered that this object can be attained by using peptides of the following formula (I) comprising 7 to 9 amino acids.

The present invention provides polypeptides of the following general formula:

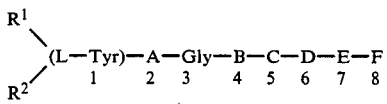

wherein $R^1$ and $R^2$ can be the same or different and each represents a hydrogen atom or a lower alkyl or lower alkenyl group; A represents a D-amino acid, Gly or Sar, provided that when the D-amino acid is D-Cys, it is bonded with L-Cys or D-Cys located in position 5 through a S—S bond to effect intramolecular ring closure; B represents L-Phe or D-Phe in which the benzene ring may be substituted or an α-N-alkyl derivative thereof; C represents an L-amino acid, D-Cys or an α-N-alkyl derivative thereof, with the proviso that when A is D-Sys, C is L-Sys or D-Sys and is bonded with A through A S—S bond, as described above; D and E each represents an L- or D-basic amino acid or an α-N-alkyl derivative thereof; F represents a group of the formula: —$OR^3$ (in which $R^3$ is H or a lower alkyl group), a group of the formula:

(in which $R^4$ and $R^5$ are the same or different and each represents H or a lower alkyl group), a group of the formula: -G-$OR^6$ (in which G is an L- or D-amino acid or Gly or an α-N-alkyl derivative thereof and $R^6$ represents H or a lower alkyl group, a group of the formula:

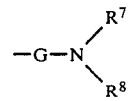

(in which G is the same as defined above and $R^7$ and $R^8$ are the same or different and each represents H or a lower alkyl group), a group of the formula: -G-(L-Arg)-$OR^9$ or -G-(D-Arg)-$OR^9$ (in which G is the same as defined above and $R^9$ represents H or a lower alkyl group), a group of the formula:

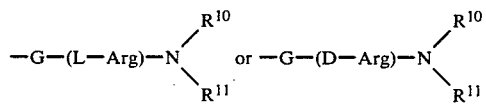

(in which G is the same as defined above and $R^{10}$ and $R^{11}$ can be the same or different and each represents H or a lower alkyl group), a group of the formula: -G-J-$OR^{12}$ in which G is defined as above, J is a neutral amino acid group or an acidic amino acid group and $R^{12}$ is hydrogen or a lower alkyl group; or a group of the formula: -G-Arg-M-$OR^{13}$ in which M is D-amino acid group and $R^{13}$ is hydrogen or a lower alkyl group, provided that all of the amino acids constituting any one given polypeptide of the above formula do not simultaneously represent an L-amino acid of the general formula:

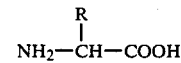

in which R represents a group corresponding to a structural formula of an amino acid deprived of a group of the formula:

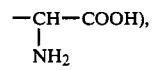

that is, at least one of the amino acids of a given polypeptide must be a D-amino acid or an N-alkyl derivative of a D- or L-amino acid, or pharmacologically acceptable salts of those polypeptides.

Examples of the pharmacologically acceptable salts herein include inorganic acid salts, such as hydrochloride, sulfate, hydrobromide and hydroiodide, as well as organic acid salts, such as maleate, fumarate, succinate, acetate, malonate, citrate and benzoate.

Accordingly, an object of the present invention is to provide new peptides useful as medicines, particularly analgesics.

Another object of the invention is to provide a process for producing new peptides useful as medicines.

Still another object of the invention is to provide new analgesics containing the new peptides.

The term "lower alkyl group" in the above-mentioned definition of $R^1$ to $R^{13}$ refers to straight-chain, branched, cyclic or ring-containing alkyl groups having 1 to 6 carbon atoms, such as methyl, ethyl, n-propyl, isopropyl, n-butyl, iso-butyl, 1-methylpropyl, tert-butyl, cyclopropylmethyl, n-pentyl, 1-ethylpropyl, isoamyl and n-hexyl groups. The term "lower alkenyl group" in the above-mentioned definition of $R^1$ and $R^2$ refers to those corresponding to the above-mentioned alkyl groups but having a double bond in some position. The term "alkyl" in the 'α-N-alkyl derivatives' in the definition of the amino acids has the same meaning as that of the above-mentioned lower alkyl group.

The compound of formula (I) of the present invention excludes those polypeptides in which all of the amino acids are L-amino acids of the general formula:

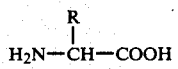

(in which R represents a group corresponding to the structural formula of an amino acid deprived of a group of the formula:

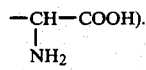

According to the invention, at least one of the constituent amino acids of the polypeptide of formula (I) is an α-N-alkylamino acid or a D-amino acid.

The compounds of the present invention in which at least one of the constituent amino acids is an α-N-alkylamino acid or a D-amino acid are free from the serious defects of dynorphin and its derivatives, namely, that they cannot exhibit any analgesic effects, as such, when they are administered by intravenous injection, because they are unstable in the blood. The compounds of the invention are highly valuable because they have a high stability in vivo and they are practically useful as analgesics.

The D-amino acids in the definition of A in the compounds (I) in the present invention are not limited. Preferred examples of them include D-Met, D-Ala, D-Ser, D-Cys and D-Thr.

The substituents in "L-Phe and D-Phe in which the benzene ring is substituted" in the definition of B are preferably a nitro group, halogen atoms, such as chlorine, bromine, iodine and fluorine, trifluoromethyl, lower alkyl and lower alkoxy groups.

The L-amino acids in the definition of C are not limited. Preferred examples of them include L-Leu, L-Ile, L-Nle, L-tert-Leu, L-Met, L-Met(O), L-Ser, L-Cys and L-Val.

Preferred examples of the L- and D-basic amino acids in the definition of D and E include L- and D-Arg, L- and D-Lys, L- and D-homo-Arg and L- and D-Orn. Further, preferred examples of these amino acids in the definition of D and E include also α-N-alkyl derivatives of these basic amino acids.

Any amino acid may constitute the amino acid group G in the formula. It preferably includes Gly, Ala, Val, Leu, Ile, Ser, Thr, Cys, Met, Asp, Glu, Asn, Gln, Pro, Lys, Orn, Arg, His, Phe, Tyr, Trp, tert.-Leu, 2-aminoisobutyric acid and α-methyl-Leu. The amino acid group for G can be in the form of the D configuration or L configuration when it contains an asymmetric carbon atom. More preferably, the amino acid group for G is L-Ile, L-Leu, L-Ala, L-Val, L-Asp, L-Pro, L-tert.-Leu, D-Ala, D-Val, D-Leu, D-Glu, D-Pro, 2-aminoisobutyric acid and α-methyl-Leu.

Any neutral amino acid and any acidic amino acid are used for J in the formula, including those of D configuration and L configuration when they have an asymmetric carbon atom. Preferable amino acids for J in formula (I) are Gly, Sar, L-Ala, D-Ala, L-Phe, D-Phe, L-Asp and D-Asp.

Any amino acid is used for M in the formula. Preferable amino acids for M in the formula (I) are D-Pro, D-Ala and D-Glu.

To facilitate an understanding of the present invention, examples of typical compounds of the present invention will be given below, which by no means limit the present invention:

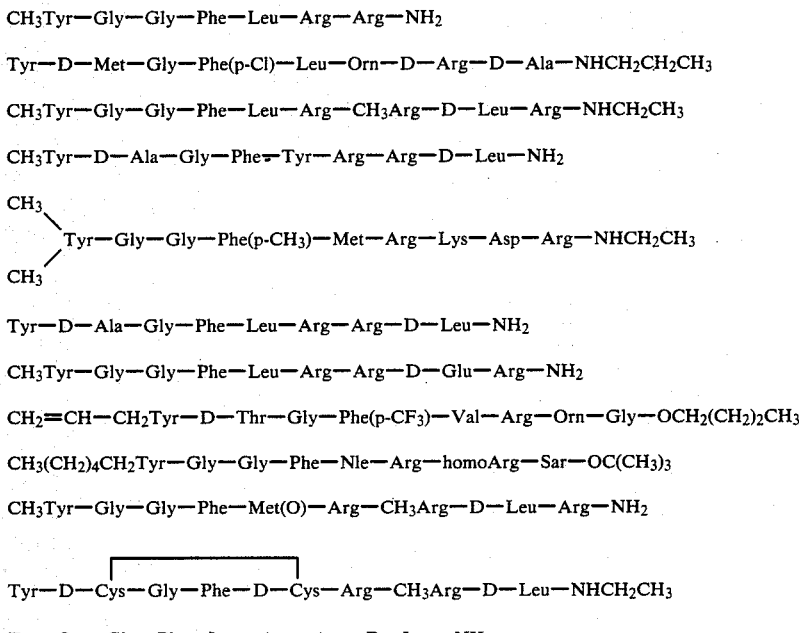

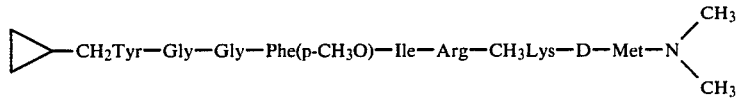-CH₂Tyr—Gly—Gly—Phe(p-CH₃O)—Ile—Arg—CH₃Lys—D—Met—N(CH₃)₂

CH₃Tyr—Gly—Gly—Phe—Leu—Arg—Arg—D—Leu—NH(CH₂)₅CH₃

CH₃CH₂Tyr—D—Arg—Gly—Phe(p-Br)—Nle—CH₃Arg—CH₃Arg—Arg—NH₂

CH₃Tyr—Gly—Gly—Phe—tert-Leu—Arg—CH₃Arg—D—Leu—NHCH₂CH₃

Tyr—D—Tyr—Gly—Phe—Glu—D—Arg—Arg—Asn—NH₂

CH₃Tyr—Gly—Gly—Phe—CH₃Leu—Arg—Arg—D—Leu—NH₂

Tyr—D—Ser—Gly—Phe—Ser—Arg—CH₃Arg—D—Leu—NHCH₂CH₃

CH₂=CH—CH₂Tyr—D—Asp—Gly—Phe(p-I)—Ala—Arg—D—Arg—Trp—OCH₂CH₃

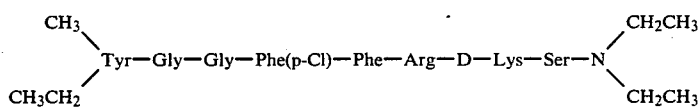
(CH₃CH₂)(CH₃)Tyr—Gly—Gly—Phe(p-Cl)—Phe—Arg—D—Lys—Ser—N(CH₂CH₃)₂

CH₃Tyr—Gly—Gly—Phe—Leu—Arg—Arg—D—Leu—Arg—NH₂

CH₃Tyr—Gly—Gly—D—Phe—Leu—Arg—Arg—D—Leu—NH₂

(CH₃)₂CH.Tyr—D—Lys—Gly—Phe—Trp—D—Lys—D—Lys—Arg—OCH₂(CH₂)₄CH₃

CH₂=CHTyr—Gly—Gly—Phe(p-NO₂)—Thr—D—Arg—D—Arg—Pro—N(CH₃)₂

CH₃Tyr—Gly—Gly—Phe—Leu—Arg—Arg—D—Leu—OH

CH₃Tyr—Gly—Gly—Phe(p-NO₂)—Leu—Arg—CH₃Arg—D—Leu—Arg—NHCH₂CH₃

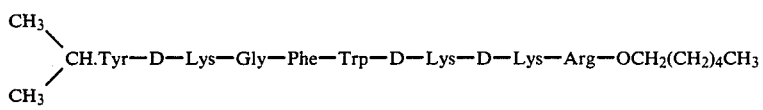
Tyr—D—Cys—Gly—Phe—Cys—Arg—CH₃Arg—D—Leu—NHCH₂CH₃

Tyr—D—Glu—Gly—Phe(p-Cl)—Asp—Arg—CH₃Orn—CH₃Ile—D—Arg—NHCH₂CH₂CH₃

CH₃CH₂Tyr—Gly—Gly—Phe—Leu—Arg—Arg—D—Phe—Arg—NH₂

CH₃Tyr—Gly—Gly—Phe—Leu—Arg—CH₃Arg—D—Ala—OH

CH₃Tyr—Gly—Gly—Phe(p-Br)—Nle—Arg—Arg—His—Arg—NH₂

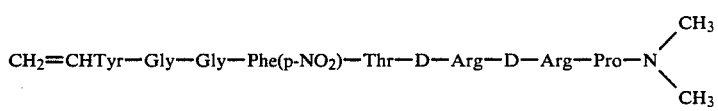
Tyr—D—Cys—Gly—Phe—Cys—Arg—D—Arg—Lys—D—Arg—NH₂

CH₃Tyr—Gly—Gly—Phe—Leu—Arg—CH₃Arg—OCH₂CH₃

CH₃—CH=CHTyr—Gly—Gly—Phe(p-NO₂)—Met—Arg—Arg—Phe—Arg—NHCH₃

CH₃Tyr—D—Ala—Gly—CH₃Phe—Met(O)—Arg—CH₃Arg—Ile—NH₂

CH₃Tyr—Gly—Gly—CH₃Phe—Leu—Arg—Arg—D—Leu—NH₂

Tyr—D—Ala—Gly—Phe—CH₃Met—Arg—Arg—Leu—Arg—NHCH₂CH₃

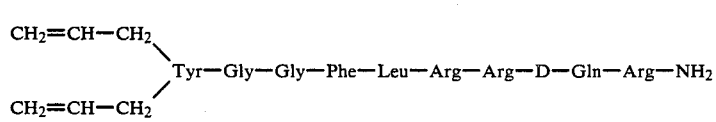
(CH₂=CH—CH₂)₂Tyr—Gly—Gly—Phe—Leu—Arg—Arg—D—Gln—Arg—NH₂

CH₃Tyr—Gly—Gly—Phe—Leu—Arg—CH₃Arg—D—Leu—OH

CH₃Tyr—Gly—Gly—Phe—Met—Lys—CH₃Lys—Met—NH₂

CH₃Tyr—Gly—Gly—Phe—Leu—Arg—Arg—D—Thr—Arg—NH₂

-continued

Tyr—D—Ser—Gly—Phe(p-F)—Leu—Arg—Arg—D—Asn—NHCH₃

CH₃Tyr—Gly—Gly—Phe—Leu—Arg—CH₃Arg—Gln—NH₂

CH₃Tyr—D—Ala—Gly—Phe—Leu—Arg—Arg—D—Leu—NH₂

Tyr—D—Ser—Gly—Phe—Pro—D—Orn—Arg—CH₃Ala—D—Arg—NH₂

Tyr—D—Ala—Gly—C₂H₅Phe(p-F)—Met—Arg—Arg—D—Trp—NH₂

CH₃Tyr—Gly—Gly—Phe—Leu—CH₃Arg—CH₃Arg—D—Lys—NH₂

CH₃Tyr—Gly—Gly—Phe—Leu—Arg—Arg—D—Leu—NHCH₂CH₃

Tyr—D—Met—Gly—Phe(p-NO₂)—Leu—D—Arg—Arg—D—Pro—Arg—OCH₂CCH₃

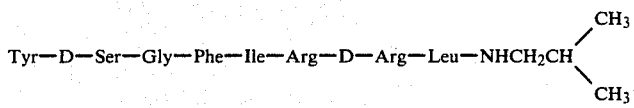

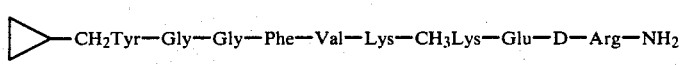

CH₃Tyr—Gly—Gly—Phe(p-NO₂)—Leu—Arg—Arg—D—Leu—NH₂

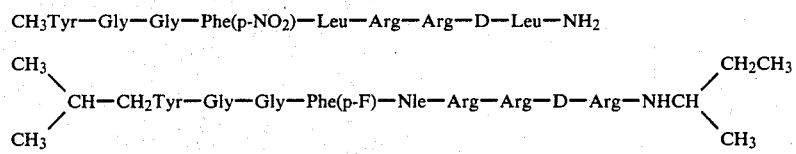

CH₃Tyr—D—Pro—Gly—Phe—tert-Leu—Orn—CH₃Orn—Met—Arg—NH₂

Tyr—D—Trp—Gly—Phe(p-NO₂)—Met—Arg—C₂H₅Arg—Ala—Arg—NHCH₃

CH₃Tyr—Gly—Gly—Phe(p-NO₂)—Leu—Arg—CH₃Arg—D—Leu—NHCH₂CH₃

Tyr—D—His—Gly—Phe—Met(O)—Lys—Arg—D—His—Arg—NH₂

CH₃Tyr—D—Leu—Gly—Phe—Leu—Arg—Arg—D—Ser—NH₂

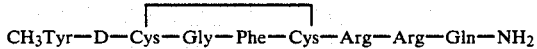
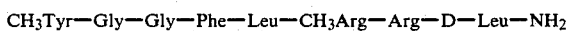
CH₃Tyr—D—Cys—Gly—Phe—Cys—Arg—Arg—Gln—NH₂

CH₃Tyr—Gly—Gly—Phe—Leu—CH₃Arg—Arg—D—Leu—NH₂

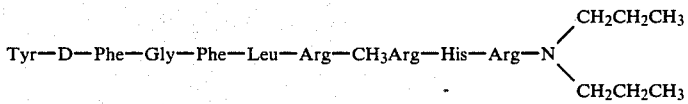

CH₃Tyr—Gly—Gly—Phe—Leu—Arg—CH₃Arg—D—Leu—NHCH₂CH₃

Tyr—D—Ser—Gly—Phe(p-Cl)—Leu—Orn—Orn—Thr—D—Arg—NH₂

CH₃Tyr—Gly—Gly—Phe—Leu—Arg—CH₃Arg—D—Leu—NH₂

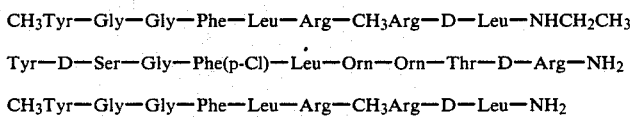

CH₃CH₂Tyr—Gly—Gly—Phe(p-F)—Met—Arg—homoArg—Gly—NHCH₃

CH₃Tyr—Gly—Gly—Phe—Leu—Arg—Arg—D—Leu—OCH₂CH₃

Tyr—D—Val—Gly—Phe(p-NO₂)—Gln—Arg—Arg—D—Val—NH₂

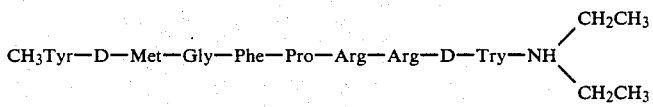
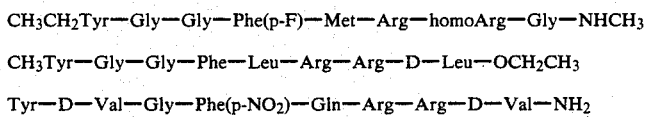
Tyr—D—Cys—Gly—Phe—Cys—Arg—CH₃Arg—D—Leu—Arg—NH₂

CH₃Tyr—Gly—Gly—Phe—Leu—Arg—Arg—NHCH₂CH(CH₃)CH₂CH₃

CH₃Tyr—Gly—Gly—Phe—Leu—Lys—CH₃Arg—D—Leu—NH₂

Tyr—Gly—Gly—Phe—Leu—Arg—CH₃Lys—Tyr—NH₂

-continued

CH₃Tyr—Gly—Gly—Phe—Met—Arg—CH₃Arg—Val—NH₂

CH₃Tyr—Gly—Gly—Phe—Leu—Arg—Arg—D—Leu—NH₂

CH₂=CH—CH₂Tyr—D—Gln—Gly—Phe—Lys—D—Arg—Arg—CH₃Leu—N(CH₂CH₃)(CH₂CH₃)

CH₃Tyr—Gly—Gly—Phe—Leu—homoArg—Arg—D—Leu—NH₂

(CH₃)(CH₃)Tyr—Gly—Gly—Phe(p-Cl)—Arg—CH₃Lys—Arg—CH₃Val—NH₂

Tyr—D—Ala—Gly—CH₃Phe—Met(O)—Arg—Arg—D—Asp—OH

CH₃Tyr—Gly—Gly—Phe—Leu—Arg—CH₃Arg—Pro—OH

CH₃Tyr—Gly—Gly—Phe—Leu—Lys—CH₃Arg—CH₃Ile—OH

CH₃Tyr—Gly—Gly—Phe—Leu—Arg—CH₃Arg—Aib—OH

CH₃Tyr—Gly—Gly—Phe—Leu—Arg—CH₃Lys—D—Ala—OH

CH₃Tyr—Gly—Gly—Phe—Leu—Arg—CH₃Arg—N(CH₃)CH₂CH₂COOH

CH₃Tyr—Gly—Gly—Phe—Leu—Lys—CH₃Lys—CH₃Val—OH

CH₃Tyr—Gly—Gly—Phe—Leu—Arg—CH₃Arg—NHCH₂CH₂CH₂COOH

CH₃Tyr—Gly—Gly—Phe—Leu—Arg—CH₃Arg—NH—C(CH₃)(CH₂CH(CH₃)₂)—COOH·CH₃

CH₃Tyr—Gly—Gly—Phe—Leu—Arg—CH₃Arg—CH₃Leu—OC₂H₅

(CH₃)(CH₃)Tyr—Gly—Gly—Phe—Leu—Arg—CH₃Arg—D—Val—Gly—OH

CH₃CH₂Tyr—Gly—Gly—Phe—Leu—Arg—CH₃Arg—D—Pro—Ala—OH

CH₃Tyr—Gly—Gly—Phe—Leu—Arg—CH₃Arg—D—Leu—Sar—OH

CH₂=CH—CH₂Tyr—Gly—Gly—Phe—Leu—Arg—CH₃Arg—CH₃Ile—D—Ala—OH

▷—CH₂—Tyr—Gly—Gly—Phe—Leu—Arg—CH₃Arg—D—Leu—Arg—D—Pro—OH

CH₃Tyr—Gly—Gly—Phe—Leu—Arg—CH₃Arg—D—Ala—OH

CH₃Tyr—Gly—Gly—Phe—Leu—Arg—CH₃Arg—CH₃Ala—OH

CH₃Tyr—Gly—Gly—Phe—Leu—Arg—CH₃Arg—Ile—OH

CH₃Tyr—Gly—Gly—Phe—Leu—Arg—CH₃Arg—Asp—OH

CH₃Tyr—Gly—Gly—Phe—Leu—Arg—CH₃Arg—D—Leu—OH

CH₃Tyr—Gly—Gly—Phe—Leu—Arg—Ch₃Arg—D—Glu—OH

CH₃Tyr—Gly—Gly—Phe—Leu—Arg—CH₃Arg—CH₃Ile—OH

CH₃Tyr—Gly—Gly—Phe—Leu—Arg—CH₃Arg—Sar—OH

CH₃Tyr—Gly—Gly—Phe—Leu—Arg—CH₃Arg—β-Ala—OH

CH₃Tyr—Gly—Gly—Phe—leu—Arg—CH₃Arg—D—Leu—Asp—OH

CH₃Tyr—Gly—Gly—Phe—Leu—Arg—CH₃Arg—D—Leu—Phe—OH

CH₃Tyr—Gly—Gly—Phe—Leu—Arg—CH₃Arg—D—Leu—Arg—D—Glu—OH

-continued

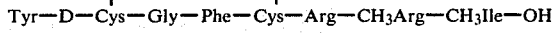
Tyr—D—Cys—Gly—Phe—Cys—Arg—CH₃Arg—CH₃Ile—OH

The peptides of the present invention can be synthesized by any suitable process. The protected peptides can be synthesized by a conventional liquid phase process or solid phase process. It is usually preferred that functional groups present in side chains of the amino acids are protected. All the protective groups are removed in the final stage. The protective groups for the functional groups in the side chains of the amino acids include all the protective groups reported in the prior art. Typical examples of them include tosyl (Tos), nitro (NO₂), benzyl (Bzl), tert-butyl (But), benzyloxycarbonyl (Z) and tert-butoxycarbonyl (BOC) groups.

As the protective groups for the α-amino groups in the amino acids, all of the protective groups reported in the prior art can be used. It is preferred, however, to select the combination of the protective groups so that the protective groups for only the α-amino groups can be removed selectively without exerting any influence on the protective groups for the functional groups in the side chains. For example, when a tert-butoxycarbonyl group is used as the protective group for the α-amino group, a benzyl or benzyloxycarbonyl group is preferred for protecting the functional group(s) in the side chain(s). When a benzyloxycarbonyl group is used for protecting the α-amino group, a tert-butyl or tertbutoxycarbonyl group is preferred for protecting the functional group(s) in the side chains(s). When the amino group of Tyr at the N-terminal is dialkylated, the amino group can be left as it is without any further protection. To inhibit racemization, the protected peptide is synthesized preferably by a stepwise process wherein all the amino acids are bonded in sequence starting from the C-terminal, or a process wherein the fragment condensation is conducted at the position of Gly. It is also possible to conduct the fragment condensation at any desired position.

In either the solid phase process or liquid phase process, according to the present invention, the protective groups are removed from the peptide and the latter is purified by repeating the reactions of the following schemes to synthesize the peptide. The steps of this process will be illustrated with reference to the liquid phase process:

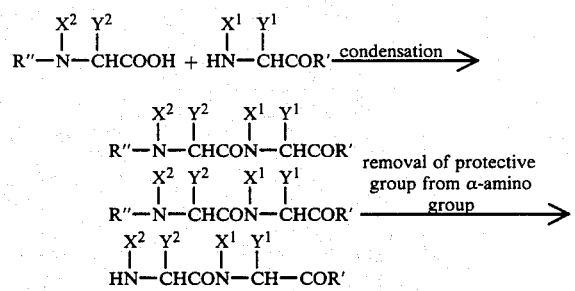

wherein $X^1$ and $X^2$ each represent H or an alkyl group, $Y^1$ and $Y^2$ each represent an amino acid side chain and $R'$ and $R''$ represent a protective group or a peptide residue.

(1) Reaction of forming a peptide bond:
The peptide bond can be formed by any of the processes reported heretofore. A conventional process comprises activating the carboxyl group of an acid component of the general formula:

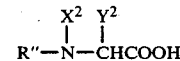

by a conventional method, such as the azide method, dicyclohexylcarbodiimide (DCC) method, mixed anhydride method or active ester method and reacting the activated compound with an amine component of the general formula:

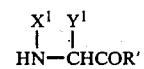

The reaction conditions, such as reaction solvent and temperature, can vary depending on the method chosen for activating the carboxyl group. The mixed anhydride method, which is one of typical condensation methods, is carried out as follows: an acid component of the general formula:

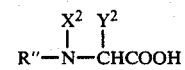

is dissolved in an aprotic solvent, such as dimethylformamide, tetrahydrofuran or ethyl acetate, the resulting solution is cooled to about −20° C. and then equimolar amounts of N-methylmorpholine and ethyl chlorocarbonate are added successively to the solution. After 5 min, an amine component of the general formula:

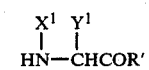

in an equimolar amount is added thereto and the mixture is stirred at −15° to 0° C. for 2 to 5 h and then treated in a conventional manner to obtain a protected peptide of the general formula:

(2) Removal of a protective group from an α-amino group:
The removal of a protective group is carried out by a conventional process, such as a catalytic reduction process, a process wherein an acid is used, a process wherein a base is used and a process wherein hydrazine is used. A preferred process is selected from among these processes depending on the type of the protective group employed for the α-amino group. Typical processes include one wherein the protective group is removed by the catalytic reduction of the benzyloxycarbonyl group and one wherein the tertbutoxycarbonyl group is removed with trifluoroacetic acid. Now, an embodiment of the process for removing the tert-butoxycarbonyl group with trifluoroacetic acid will be described in detail: 0.25 ml of anisole and 5 ml of trifluoroacetic acid are added to 1 g of an α-N-butoxycarbonyl-peptide of the general formula:

under cooling with ice. The mixture is stirred for 60 min and then treated with ether to obtain a trifluoroacetate of a peptide of the general formula:

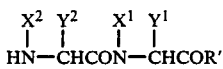

This product is dissolved in a solvent and neutralized with an amine, such as triethylamine, to obtain a compound to be subjected to the subsequent reaction.

(3) Removal of all the protective groups:

After repeating the above-mentioned condensation and removal of the protective groups for the α-amino groups in order to elongate the peptide chain, all the protective groups are removed to obtain the intended crude peptide. The protective groups are removed by a conventional process, such as a catalytic reduction process, a process wherein a liquid ammonia/alkali metal is used, a process wherein an acid is used, a process wherein a base is used or a process wherein hydrazine is used. In practice, the process is selected depending on the type of the protective group that is to be removed. One of the frequently employed processes comprises removing the protective group with hydrogen fluoride (HF) as follows:

1 g of a protected peptide is dissolved in about 30 ml of HF, in the presence of 0.5 ml of anisole, at $-15°$ to $0°$ C., in a closed reaction vessel. The solution is stirred for 60 min and HF is distilled out of the reaction system. The residue is washed with ether and dissolved in water. The solution is treated with Amberlite IRA-93 (acetic acid type) and freeze-dried to obtain a crude peptide from which the protective groups have been removed.

(4) Purification of crude peptide:

The crude peptide may be purified by a conventional process such as ion exchange chromatography, gel filtration, partition chromatography, counter current distribution and high performance liquid chromatography. The purification is conducted by, for example, the following high performance liquid chromatography: 100 mg of the crude peptide is charged in a column having a diameter of 20 mm and a height of 250 mm containing Nucleosil 5 c 18 as the carrier and then eluted with 0.05% HCl ($H_2O$—$CH_3CN$) Fractions having peaks corresponding to the intended peptide were collected by detection at UV 210 nm and freeze-dried to obtain the intended peptide.

When the peptide contains two Cys or D-Cys units in the molecule, the crude peptide is oxidized by a conventional oxidation process with air or hydrogen peroxide prior to the purification so as to obtain a ring-closed product having a high purity.

The results of the following animal tests will further illustrate the effects of the compounds of the present invention used as medicines.

TEST 1

Analgesic Tests

A test compound was dissolved in physiological saline. Male ddY strain mice (20–27 g body weight, usually studied in groups of 8) were treated with the test compound which was administered intravenously or subcutaneously. The analgesic activities were measured by the tail pinch test.

In the tail pinch test (1), a clip, exerting a pressure of 300 g, was placed at the base of the tail including the anal mucosa, and the latencies of biting of the clip were measured. Animals were screened for tail clip nociperception before the experiments and those mice that did not bite within 3 sec were eliminated from the experiments. A latency of more than 6 sec was used as the criterion for analgesia.

The $ED_{50}$ values (50% analgesically effective dose) were calculated by the method of Litchfield and Wilcoxon 2). The results are shown in Tables 1 and 2. Table 1 shows the results obtained by intravenous injection. Table 2 shows the results obtained by the subcutaneous injection.

The numerals in the column entitled "Test Compound" in Tables 1 and 2 correspond to those of the final compounds produced in the examples given below.

TABLE 1

| Intravenous Injection | |
|---|---|
| Test Compound (Example No.) | Tail Pinch Method (i.v.) $ED_{50}$ (mg/Kg) |
| 1 | 0.75 |
| 2 | 0.24 |
| 5 | 3.4 |
| 6 | 4.3 |
| 7 | 3.9 |
| 8 | 3.3 |
| 10 | 1.2 |
| 18 | 4.5 |
| 19 | 2.0 |
| 21 | 0.8 |
| 22 | 3.0 |
| 24 | 0.22 |
| 25 | 1.8 |
| 27 | 0.7 |
| 28 | 0.7 |
| 29 | 2.0 |
| dynorphin (1-13) | >25.0 |

TABLE 2

| Subcutaneous Injection | |
|---|---|
| Test Compound (Example No.) | Tail Pinch (S.C.) $ED_{50}$ (mg/Kg) |
| 1 | 1.0 |
| 2 | 0.44 |
| 21 | 0.8 |
| 24 | 0.32 |
| 27 | 0.8 |
| 28 | 1.5 |

(Note 1) The tail pinch method was conducted according to Takagi, H., et al, "Jap. J. Pharmacol.", Vol. 16, 287 to 294 (1966).
(Note 2) The method of Litchfield—Wilcoxon was conducted according to Litchfield, J. T., and F. Wilcoxon, "J. Pharmacol. Exp. Ther.", Vol. 96, 99 to 113 (1949).

TEST 2

Opioid Activity

The opioid activities of the compounds of the invention were examined by the method using rabbit vas deferens according to T. Oka, K. Negishi, M. Suda, T.

Matsumiya, T. Inaza and M. Ueki, "Europ. J. Pharmacol.", Vol. 73, 235 (1980). In this test, mature male rabbits were sacrificed by introducing air into an optic vein. Immediately after death, a laparotomy was conducted and right and left vasa deferens were removed. The semen was pressed out of the ducts into Ringer's solution. A part of each duct was cut (2.5 m long from an end of the prostrate gland side). The pieces of the deferentaial ducts were suspened by means of a thread in a 6 ml constant-temperature glass cell and stimulated electrioally with an electric stimulation device having platinum electrodes under conditions of 0.1 Hz, 1 ms and 90 volt. A contraction due to the electric stimulation was recorded through a transducer.

The opioid activity was determined on the basis of the inhibition of the contraction due to the electric stimulation.

The results are shown in Table 3 in terms of 50% inhibitation concentration ($IC_{50}$).

TABLE 3

| Test Compound (Example No.) | Rabbit vas deferens Method $IC_{50}$ (nM) |
| --- | --- |
| 1 | 3.5 |
| 2 | 0.04 |
| 3 | 6.03 |
| 6 | 4.5 |
| 8 | 6.2 |
| 19 | 2.8 |
| 24 | 0.08 |
| 25 | 0.58 |
| 27 | 2.0 |
| 28 | 6.5 |
| dynorphin A (1-17) | 17.4 |

It is apparent from Table 3 that the compounds of the present invention exhibit a very potent activity as compared with dynorphin A.

Furthermore, they have strong activities of inhibiting the contraction of ileal longitudinal muscles of a guinea pig and deferential ducts of a mouse caused by the electric stimulation.

It is apparent from the above-mentioned pharmacological test results that the peptide compounds obtained by the present invention have opioid activities similar to those of dynorphin, their effects are quite strong and remarkable analgesic effects are exhibited by intravenous injection or subcutaneous injection.

It is highly valuable that the compounds of the present invention exhibit strong analgesic effects upon systemic administration by intravenous or subcutaneous injection, whereas dynorphin and its derivatives so far reported, scarcely exhibit analgesic effects upon intravenous injection because they are unstable in the blood.

The relationship between the toxicity (minimum lethal dose) of the peptide compound obtained in Examples 1 and 2 of the present invention and the effective dose is shown in Table 4.

TABLE 4

| Effective dose and minimum lethal dose when administered subcutaneously in mice | | |
| --- | --- | --- |
| Test Compound (Example No.) | Tail Pinch $ED_{50}$ (mg/Kg) | Minimum Lethal Dose (mg/Kg) |
| Example 1 | 1.0 | 100 |
| Example 2 | 0.44 | 20 |

The peptide compounds obtained by the process of the present invention have remarkable analgesic effects and they are useful as medicines in the therapeutical field.

In using the compounds of the present invention as analgesics, they are given by peroral or parenteral administration. Usually, they are given parenterally in the form of intravenous, subcutaneous or intramuscular injection or suppositories or sublingual tablets. The dosage varies depending on the severity of the symptoms, age of the patient, sex, body weight, sensitivity, administration manner, stage of the disease, intervals, properties of the medical preparation, formulation, type of preparation and type of the active ingredient. Although the dosage is thus not particularly limited, it is usually about 0.1 to 1,000 mg/day, preferably about 1 to 300 mg/day, for adult human beings.

The compounds of the present invention can be formulated into injections, suppositories, sublingual tablets, tablets and capsules by conventional processes used in the field of pharmacology.

In the preparation of an injection, additives such as a pH controller, buffering agent, suspending agent, solubilizer, stabilizer, isotonizing agent and preservative are added to the active ingredient and the obtained mixture is formulated into an intravenous, subcutaneous or intramuscular injection liquid by a conventional method. If necessary, the mixture may be lyophilized by conventional methods.

Examples of the suspending agents include methylcellulose, Polysorbate 60, hydroxyethylcellulose, acacia, tragacanth powder, sodium carboxymethylcellulose and polyoxyethylene sorbitan monolaurate.

Examples of the solubilizers include polyoxyethylene hardened castor oil, Polysorbate 80, nicotinamide, polyoxyethylene sorbitan monolaurate, macrogol and ethyl esters of castor oil fatty acids.

Examples of the stabilizers include sodium sulfite, sodium metasulfite and ethers. Examples of the preservatives include methyl p-hydroxybenzoate, ethyl p-hydroxybenzoate, sorbic acid, phenol, cresol and chlorocresol.

The present invention will be illustrated with reference to the following typical examples, which by no means limit the invention.

EXAMPLE 1

(1) Synthesis of $CH_3$Tyr-Gly-GlY-Phe-Leu-Arg-$CH_3$Arg-D-Leu-$NHC_2H_5$ 25 g of Boc-D-Leu-OH.$H_2O$ was dissolved in 200 ml of THF. The solution was cooled to $-20°$ C. 11 ml of N-methylmorpholine and 9.56 ml of ethyl chlorocarbonate were added to the solution. After 5 min, 12.9 g of a 70% aqueous ethylamine solution was added thereto and the mixture was stirred at about $-5°$ C. for 2 h. After concentration, the residue was dissolved in ethyl acetate and washed with an aqueous $NaHCO_3$ solution and water successively. After concentration to dryness, 24.5 g of Boc-D-Leu-$NHC_2H_5$ was obtained.

m.p.: 103°–106° C.

TLC: Rf value 0.77 (ethyl acetate)

Optical rotation: $[\alpha]_D = +20.0°$ (C=1, methanol)

Elementary analysis for $C_{13}H_{26}N_2O_3$:

| | C | H | N |
| --- | --- | --- | --- |
| calculated (%) | 60.44 | 10.14 | 10.84 |

-continued

| | C | H | N |
|---|---|---|---|
| found (%) | 60.42 | 10.33 | 10.86 |

(2) Synthesis of Z-CH$_3$Arg(Tos)-D-Leu-NHC$_2$H$_5$ 1.43 g of Z-CH$_3$Arg(Tos)—OH, $[\alpha]_D = -15°$ (C=1, dimethylformamide), synthesized from H-Arg(Tos)-OH according to a process of P. Quitt et al. [Helvetica Chimica Acta, 32, 327 (1963)] was dissolved in 15 ml of tetrahydrofuran. After cooling to −30° C., 0.33 ml of N-methylmorpholine and 0.29 ml of ethyl chlorocarbonate were added to the solution. After 5 min, a solution of 817 mg of CF$_3$COOH.H-D-Leu-NHC$_2$H$_5$ (synthesized by treating Boc-D-Leu-NHC$_2$H$_5$ with CF$_3$COOH in the presence of anisole) and 0.83 ml of triethylamine in 7 ml of tetrahydrofuran was added thereto and the mixture was stirred about −5° C. for 2 h. After concentration, the residue was dissolved in ethyl acetate, washed with an aqueous NaHCO$_3$ solution and water successively and concentrated to dryness to obtain 1.58 g of glassy Z-CH$_3$Arg(Tos)-D-Leu-NHC$_2$H$_5$.

TLC: Rf value 0.68 (methanol/chloroform, 1:7)
Optical rotation: $[\alpha]_D = 0 \pm 0.5°$ (C=1, methanol)
Elementary analysis for C$_{30}$H$_{44}$N$_6$O$_6$S:

| | C | H | N |
|---|---|---|---|
| calculated (%) | 58.42 | 7.19 | 13.63 |
| found (%) | 58.29 | 7.19 | 13.40 |

(3) Synthesrs of Boc-Arg(Tos)-CH$_3$Arg(Tos)-D-Leu-NHC$_2$H$_5$ 1.1 g of CH$_3$Arg(Tos)-D-Leu-NHC$_2$H$_5$ obtained by catalytic reduction of Z-CH$_3$Arg(Tos)-D-Leu-NHC$_2$H$_5$ in the presence of Pd/C, 983 mg of Boc-Arg Tos)-OH and 372 mg of N-hydroxybenzotriazole were dissolved in 4 ml of dimethylformamide. 520 mg of dicyclohexylcarbodiimide was added to the solution under cooling with ice and the mixture was stirred in a refrigerator for one day and then at room temperature for one day. Precipitates thus formed were filtered out and the filtrate was concentrated. The concentration residue was purified according to silica gel column chromatography (eluent: MeOH/CHCl$_3$=1/15) to obtain 1.2 g of glassy Boc-Arg(Tos)-CH$_3$Arg(Tos)-D-Leu-NHC$_2$H$_5$.

TLC: Rf value 0.64 (methanol/chloroform, 1:7)
Optical rotation: $[\alpha]_D = -20.6°$ (C=1, methanol)
Elementary analysis for C$_{40}$H$_{64}$N$_{10}$O$_9$S$_2$-H$_2$O:

| | C | H | N |
|---|---|---|---|
| calculated (%) | 52.72 | 7.30 | 15.37 |
| found (%) | 52.82 | 7.22 | 15.06 |

(4) Synthesis of Boc-Leu-Arg(Tos)-CH$_3$Arg(Tos)-D-Leu-NHC$_2$H$_5$ 1.465 g of Boc-Leu-OH.H$_2$O was dissolved in 12 ml of dimethylformamide. The solution was cooled to −20° C. 0.726 ml of N-methylmorpholine and 0.631 ml of ethyl chlorocarbonate were added to the solution. After 5 min, a solution of 4.986 g of CF$_3$COOH.H-Arg(Tos)CH$_3$Arg(Tos)-D-Leu-NHC$_2$H$_5$, synthesized by treating Boc-Arg(Tos)-CH$_3$Arg(Tos)-D-Leu-NHC$_2$H$_5$ with CF$_3$COOH in the presence of anisole, and 0.726 ml of N-methylmorpholine in 12 ml of dimethylformamide was added to the solution and the mixture was stirred at about −5° C. for 2 h. After concentration, the residue was dissolved in ethyl acetate and the solution was washed with an aqueous NaHCO$_3$ solution and then with water. After concentration followed by solidification with methanol/ether, 5.283 g of Boc-Leu-Arg(Tos)-CH$_3$Arg(Tos)-D-Leu-NHC$_2$H$_5$ was obtained.

m.p.: 120°–125° C. (dec)
TLC: Rf value 0.66 (methanol/chloroform, 1:7)
Optical rotation: $[\alpha]_D = -25.8°$ (C=1, methanol)
Elementary analysis for C$_{46}$H$_{75}$N$_{11}$O$_{10}$S$_2$.CH$_3$OH:

| | C | H | N |
|---|---|---|---|
| calculated (%) | 54.36 | 7.67 | 14.84 |
| found (5) | 54.49 | 7.63 | 14.62 |

(5) Synthesis of Boc-Phe-Leu-Arg(Tos)-CH$_3$Arg(Tos)-D-Leu-NHC$_2$H$_5$ 1.465 g of Boc-Phe-OH was dissolved in 12 ml of dimethylformamide. The solution was cooled to −30° C. 0.608 ml of N-methylmorpholine and 0.528 ml of ethyl chlorocarbonate were added to the solution. After 5 min, a solution of 4.691 g of CF$_3$COOH.H-Phe-Leu-Arg(Tos)-CH$_3$Arg(Tos)-D-Leu-NHC$_2$H$_5$, synthesized by treating Boc-Phe-Leu-Arg(Tos)-CH$_3$Arg(Tos)-D-Leu-NHC$_2$H$_5$ with CF$_3$COOH in the presence of anisole, and 0.608 ml of N-methylmorpholine in 12 ml of dimethylformamide was added to the solution and the mixture was stirred at about −5° C. for 2 h. After concentration, the residue was dissolved in ethyl acetate and the solution was washed with an aqueous NaHCO$_3$ solution and water successively. After concentration followed by solidification with methanol/ether, 5.072 g of Boc-Phe-Leu-Arg(Tos)-CH$_3$Arg(Tos)D-Leu-NHC$_2$H$_5$ was obtained.

m.p.: 127°–132° C.
TLC: Rf value 0.66 (methanol/chloroform, 1:7)
Optical rotation: $[\alpha]_D = -25.4°$ (C=1, methanol)
Elementary analysis for C$_{55}$H$_{84}$N$_{12}$O$_{11}$S$_2$.CH$_3$OH:

| | C | H | N |
|---|---|---|---|
| calculated (%) | 56.74 | 7.48 | 14.18 |
| found (%) | 56.64 | 7.33 | 13.86 |

(6) Synthesis of Boc-CH$_3$Tyr(Cl$_2$Bzl)-Gly-Gly-OH 9.09 g of Boc-CH$_3$Tyr(Cl$_2$Bzl)OH, $[\alpha]_D = -49°$ (C=1, C$_2$H$_5$OH), synthesized by a process of S. T. Cheung et al [Can. J. Chem., 55, 906 (1977)] and 2.53 g of N-hydroxysuccinimide were dissolved in 150 ml of tetrahydrofuran. After cooling with ice, 4.12 g of dicyclohexylcarbodiimide was added to the solution and the mixture was stirred overnight in a refrigerator. White crystals thus formed were filtered out and 2.91 g of H-Gly-Gly-OH and 38 ml of an aqueous solution of 1.848 g of NaHCO$_3$ were added to the filtrate. The mixture was stirred at room temperature for 2 days and then concentrated. A dilute aqueous citric acid solution and ethyl acetate were added thereto and an ethyl acetate layer was separated. After washing with water followed by concentration, the product was purified according to silica gel column chromatography eluted with MeOH/CHCl$_3$=1/30 and solidified with ether/n-hexane to obtain 9.23 g of Boc-CH$_3$Tyr(Cl$_2$Bzl)-Gly-Gly-OH.

m.p.: 70°–80° C. (dec)

TLC: Rf value 0.79 (methanol/acetic acid/chloroform, 4:1:12)

Optical rotation [α]$_D$= −47° (C=1, methanol)

Elementary analysis for C$_{26}$H$_{31}$N$_3$O$_7$Cl$_2$.½C$_2$H$_5$OC$_2$H$_5$:

|  | C | H | N |
|---|---|---|---|
| calculated (%) | 55.54 | 5.99 | 6.94 |
| found (%) | 55.45 | 5.81 | 6.89 |

(7) SYnthesis of Boc-CH$_3$Tyr(Cl$_2$Bzl)-Gly-Gly-Phe-Leu-Arg(Tos)-CH$_3$Arg(Tos)-D-Leu-NHC$_2$H$_5$ 682 mg of Boc-CH$_3$TYr(Cl$_2$Bzl)-Gly-Gly-OH and 195 mg of N-hydroxybenzotriazole were dissolved in 4 ml of dimethylformamide. 272 mg of dicyclohexylcarbodiimide was added to the solution under cooling with ice. After stirring for 2 h, a solution of 1.167 g of CF$_3$COOH.H-Phe-Leu-Arg(Tos)-CH$_3$Arg(Tos)-D-Leu-NHC$_2$H$_5$, synthesized by treating Boc-Phe-Leu-Arg(Tos)-CH$_3$Arg(Tos)-D-Leu-NHC$_2$H$_5$ with CF$_3$COOH in the presence of anisole, and 0.132 ml of N-methylmorpholine in 8 ml of dimethylformamide was added to the solution and the mixture was stirred in a refrigerator overnight. A precipitate thus formed was filtered out and the filtrate was concentrated and purified according to silica gel column chromatography (eluent: MeOH/CHCl$_3$=1/20). After solidification with methanol/ether, 1.391 g of Boc-CH$_3$Tyr(Cl$_2$Bzl)-Gly-Gly-Phe-Leu-Arg(Tos)CH$_3$Arg(Tos)-D-Leu-NHC$_2$H$_5$ was obtained.

m.p.: 130°–135° C. (dec)

TLC: Rf value 0.64 (methanol/chloroform, 1:7)

Optical rotation: [α]$_D$= −35.3° (C=1, methanol)

Elementary analysis for C$_{76}$H$_{105}$N$_{15}$O$_{15}$S$_2$Cl$_2$.CH$_3$OH.H$_2$O:

|  | C | H | N |
|---|---|---|---|
| calculated (%) | 55.92 | 6.77 | 12.70 |
| found (%) | 56.06 | 6.49 | 12.52 |

8 Synthesis of CH$_3$Tyr-Gly-Gly-Phe-Leu-Arg-CH$_3$Arg-D-Leu-NHC$_2$H$_5$ 220 mg of Boc-CH$_3$Tyr(Cl$_2$Bzl)-Gly-GlY-Phe-Leu-Arg(Tos)-CH$_3$Arg(Tos)-D-Leu-NHC$_2$H$_5$ was dissolved in 10 ml of hydrogen fluoride (HF) in the presence of 0.2 ml of anisole in a closed HF reaction vessel at −5° C. The solution was stirred for 1 h and then HF was distilled out of the reaction system. The residue was washed with ether and dissolved in water. The solution was treated with Amberlite IRA-93 (acetic acid type) and freeze-dried. 120 mg of a crude peptide thus obtained was purified according to high performance liquid chromatography [Nucleosil 5 C 18, 2 φ×25 cm, eluted with 0.1% HCl (H$_2$O-CH$_3$CN, 81/91)] and then freeze-dried to obtain 70 mg of CH$_3$Tyr-Gly-Gly-Phe-Leu-Arg-CH$_3$Arg-D-Leu-NHC$_2$H$_5$.

TLC: Rf value 0.70 (butanol/acetic acid/pyridine water, 15:5:5:8)

Optical rotation: [α]$_D$= −21.8° (C=0.4, 0.01 N−HCl)

M.S. (FAB): 1036 ([M+H]+)

Amino acid analysis: Gly 1.87(2); Leu 1.96(2); Phe 1.00(1); Arg 0.95(1).

(peaks due to CH$_3$Tyr and CH$_3$Arg were not calculated.)

EXAMPLE 2

Synthesis of Tyr—D—Cys—Gly—Phe—Cys—Arg—CH$_3$Arg—D—Leu—Arg—NH$_2$
(with disulfide bridge between the two Cys)

(1) Synthesis of Boc-D-Leu-Arg(Tos)-NH$_2$ 2.493 g of Boc-D-Leu-OH.H$_2$O was dissolved in 10 ml of dimethylformamide. The solution was cooled to −20° C. 1.1 ml of N-methylmorpholine and 0.96 ml of ethyl chlorocarbonate were added to the solution. After 5 min, a solution of 4.414 g of CF$_3$COOH.H-Arg(Tos)-NH$_2$ and 1.65 ml of N-methylmorpholine in 20 ml of dimethylformamide was added thereto and the mixture was stirred at about −5° C. for 2 h. After concentration, the residue was dissolved in ethyl acetate and washed with NaHCO$_3$ and water successively. After concentration, ether was added thereto to solidify the product. Thus, 4.96 g of Boc-D-Leu-Arg(Tos)-NH$_2$ was obtained.

m.p.: 110°–120° C. (dec)

TLC: Rf value 0.49 (methanol/chloroform, 1:7)

Optical rotation: [α]$_D$= +13.0° (C=1, methanol)

Elementary analysis for C$_{24}$H$_{40}$N$_6$O$_6$S. 1/3H$_2$O:

|  | C | H | N |
|---|---|---|---|
| calculated (%) | 52.73 | 7.50 | 15.37 |
| found (%) | 52.77 | 7.60 | 15.14 |

(2) Synthesis of Z-CH$_3$Arg(Tos)-D-Leu-Arg(Tos)-NH$_2$ 3.336 g of Z-CH$_3$Arg(Tos)-OH was dissolved in 30 ml of tetrahydrofuran. The solution was cooled to −20° C. 0.77 ml of N-methylmorpholine and 0.67 ml of ethyl chlorocarbonate were added to the solution. After 5 min, a solution of 3.882 g of CH$_3$COOH.H-D-Leu-Arg(Tos)-NH$_2$ synthesized by treating Boc-D-Leu-Arg(Tos)-NH$_2$ with CF$_3$COOH in the presence of anisole, and 1.17 ml of triethylamine in 30 ml of tetrahydrofuran was added to the solution and the mixture was stirred at about −5° C. for 2 h. After concentration followed by solidification with methanol/water, 6.14 g of Z-CH$_3$Arg(Tos)-D-Leu-Arg(Tos)-NH$_2$ was obtained.

m.p. 100°–113° C. (dec)

TLC: Rf value 0.44 (methanol/chloroform, 1:7)

Optical rotation: [α]$_D$= −3.4° (C=1, methanol)

Elementary analysis for C$_{41}$H$_{58}$N$_{10}$O$_9$S$_2$.CH$_3$OH:

| | C | H | N |
|---|---|---|---|
| calculated (%) | 54.18 | 6.71 | 15.04 |
| found (%) | 54.12 | 6.62 | 14.85 |

(3) Synthesis of Boc-Arg(Tos)-CH$_3$Arg(Tos)-D-Leu-Arg(Tos)-NH$_2$ 4.734 g of CH$_3$Arg(Tos)-D-Leu-Arg(Tos)-NH$_2$ obtained by catalytically reducing Z-CH$_3$Arg(Tos)-D-Leu-Arg(Tos)-NH$_2$ in the presence of Pd/C, 2.918 g of Boc-Arg(Tos)OH and 1.1 g of N-hydroxybenzotriazole were dissolved in 17 ml of dimethylformamide. 1.543 g of dicyclohexylcarbodiimide was added to the solution under cooling with ice and the mixture was stirred in a refrigerator for one day and then at room temperature for one day. A precipitate thus formed was filtered out and the filtrate was concentrated. The residue was purified according to silica gel column chromatography (eluted with MeOH/CHCl$_3$=1/15) and solidified with ether to obtain 4.917 g of Boc-Arg(Tos)-CH$_3$Arg(Tos)-D-Leu-Arg(Tos)-NH$_2$.

m.p.: 131°–136° C. (dec)
TLC: Rf value 0.44 (methanol/chloroform, 1:7)
Optical rotation $[\alpha]_D = -16.7°$ C.=1, methanol)
Elementary analysis for C$_{51}$H$_{78}$N$_{14}$O$_{12}$S$_3$.H$_2$O:

| | C | H | N |
|---|---|---|---|
| calculated (%) | 51.32 | 6.76 | 16.43 |
| found (%) | 51.15 | 6.54 | 16.48 |

(4) Synthesis of Boc-Cys(CH$_3$Bzl)-Arg(Tos)-CH$_3$Arg(Tos)-D-Leu-Arg(Tos)-NH$_2$ 747 mg of Boc-Cys(CH$_3$Bzl)-OH was dissolved in 4 ml of dimethylformamide. The solution was cooled to −20° C. 0.254 ml of N-methylmorpholine and 0.221 ml of ethyl chlorocarbonate were added thereto. After 5 min, a solution of 2.497 g of CF$_3$COOH.H-Arg(Tos)-CH$_3$Arg(Tos)-D-Leu-Arg(Tos)-NH$_2$, synthesized by treating Boc-Arg(Tos)-CH$_3$Arg(Tos)-D-Leu-Arg(Tos)-NH$_2$ with CF$_3$COOH in the presence of anisole, and 0.277 ml of N-methylmorpholine in 6 ml of dimethylformamide was added to the solution and the mixture was stirred at about −5° C. for 2 h. After concentration, the mixture was dissolved in ethyl acetate and then washed with NaHCO$_3$ and water successively. After further concentration, the product was solidified with methanol/ether to obtain 2.548 g of Boc-Cys(CH$_3$Bzl)-Arg(Tos)-CH$_3$Arg(Tos)-D-Leu-Arg(Tos)-NH$_2$.

m.p.: 126°–132° C. (dec)
TLC: Rf value 0.51 (methanol/chloroform, 1:7)
Optical rotation $[\alpha]_D = -20.6°$ (C=1, methanol)
Elementary analysis for C$_{62}$H$_{91}$N$_{15}$O$_{13}$S$_4$.CH$_3$OH.H$_2$O:

| | C | H | N |
|---|---|---|---|
| calculated (%) | 52.81 | 6.82 | 14.66 |
| found (%) | 52.78 | 6.43 | 14.29 |

(5) Synthesis of Boc-Phe-Cys(CH$_3$Bzl)-Arg(Tos)-CH$_3$Arg(Tos)-D-Leu-Arg(Tos)-NH$_2$ 467 mg of Boc-Phe-OH was dissolved in dimethylformamide. The solution was cooled to −20° C. 0.194 ml of N-methylmorpholine and 0.168 ml of ethyl chlorocarbonate were added to the solution. After 5 min, a solution of 2.234 g of CF$_3$COOH.H-Phe-Cys(CH$_3$Bzl)-Arg(Tos)-CH$_3$Arg(Tos)-D-Leu-Arg(Tos)-NH$_2$, synthesized by treating Boc-Phe-Cys(CH$_3$Bzl)-Arg(Tos)-CH$_3$Arg(Tos)D-Leu-Arg(Tos)-NH$_2$ with CF$_3$COOH in the presence of anisole, and 0.211 ml of N-methylmorpholine in 5 ml of dimethylformamide was added to the solution and the mixture was stirred at about −5° C. for 2 h. After concentration, the residue was dissolved in ethyl acetate and the solution was washed with an aqueous NaHCO$_3$ solution and water successively. After further concentration, the product was solidified with methanol/ether to obtain 2.126 g of Boc-PheCys-(CH$_3$Bzl)-Arg(Tos)-CH$_3$Arg(Tos)-D-Leu-Arg(Tos)-NH$_2$.

m.p.: 124°–130° C. (dec)
TLC: Rf value 0.56 (methanol/chloroform, 1:7)
Optical rotation: $[\alpha]_D = -18.9°$ (C=1, methanol)
Elementary analysis for C$_{71}$H$_{100}$N$_{16}$O$_{14}$S$_4$.5/2CH$_3$OH:

| | C | H | N |
|---|---|---|---|
| calculated (%) | 54.83 | 6.89 | 13.91 |
| found (%) | 54.62 | 6.34 | 13.64 |

(6) Synthesis of Boc-D-Cys(CH$_3$Bzl)-Gly-OC$_2$H$_5$ 3.233 g of Boc-D-Cys(CH$_3$Bzl)OH was dissolved in 15 ml of dimethylformamide. The solution was cooled to −20° C. 1.1 ml of N-methylmorpholine and 0.956 ml of ethyl chlorocarbonate were added to the solution. After 5 min, a solution of 1.396 g of HCl.H-Gly-OC$_2$H$_5$ and 1.1 ml of N-methylmorpholine in 20 ml of dimethylformamide was added to the solution and the mixture was stirred at about −5° C. for 2 h. After concentration, the residue was dissolved in ethyl acetate and the solution was washed with an aqueous NaHCO$_3$ solution and water successively. After concentration, n-hexane was added thereto to solidify the product. Thus, 3.6 g of Boc-D-Cys-Gly-OC$_2$H$_5$ was obtained.

m.p.: 80°–82° C.
TLC: Rf value 0.74 (chloroform/ethyl acetate, 2:1)
Optical rotation: $[\alpha]_D = +30.2°$ (C=1, methanol)
Elementary analysis for C$_{20}$H$_{20}$H$_{30}$N$_2$O$_5$S:

| | C | H | N |
|---|---|---|---|
| calculated (%) | 58.51 | 7.37 | 6.82 |
| found (%) | 58.35 | 7.23 | 6.69 |

(7) Synthesis of Boc-Tyr(Cl$_2$Bzl)-D-Cys(CH$_3$Bzl)-Gly-OC$_2$H$_5$ 2.068 g of Boc-Tyr(Cl$_2$Bzl)-OH was dissolved in 20 ml of tetrahydrofuran. The solution was cooled to −20° C. 0.517 ml of N-methylmorpholine and 0.45 ml of ethyl chlorocarbonate were added to the solution. After 5 min, a solution of 1.94 g of CF$_3$COOH -H-D-Cys(CH$_3$Bzl)-Gly-OC$_2$H$_5$, synthesized by treating Boc- D-Cys(CH$_3$Bzl)-Gly-OC$_2$H$_5$ with CF$_3$COOH in the presence of anisole, and 1 ml of triethylamine in 20 ml of tetrahydrofuran was added to the solution and the mixture was stirred at about −5° C. for 2 h. After concentration, water was added thereto to form a precipitate, which was filtered and dissolved in a mixture of methanol and chloroform. After concentration, ether was added thereto to solidify the product. Thus, 2.661 g of Boc-Tyr(Cl$_2$Bzl)-D-Cys(CH$_3$Bzl)-Gly-OC$_2$H$_5$ was obtained.

m.p.: 149°–150° C.

TLC: Rf value 0.63 (chloroform/ethyl acetate, 2:1)

Optical rotation: [α]$_D$= +17.0° (C=1, dimethylformamide)

Elementary analysis for: C$_{36}$H$_{43}$N$_3$O$_7$SCl$_2$:

|  | C | H | N |
|---|---|---|---|
| calculated (%) | 59.01 | 5.91 | 5.73 |
| found (%) | 58.94 | 5.75 | 5.62 |

(8) Synthesis of Boc-Tyr(Cl$_2$Bzl)-D-Cys(CH$_3$Bzl)-Gly-OH 2.345 g of Boc-Tyr(Cl$_2$)-D-Cys(CH$_3$Bzl)-Gly-OC$_2$H$_5$ was dissolved in 30 ml of tetrahydrofuran and then 3.2 ml of N-NaOH was added thereto. The mixture was stirred at room temperature for 1 h. 3.2 ml of N-HCl was added to the mixture. The resulting mixture was concentrated. Water was added thereto to solidify the product. Thus, 1.899 g of Boc-Tyr(Cl$_2$Bzl)-D-Cys(CH$_3$Bzl)-Gly-OH was obtained.

m.p.: 133°–138° C. (dec)

TLC: Rf value 0.25 (methanol/chloroform, 1:7)

Optical rotation: [α]$_D$= +35.8° (C=1, methanol)

Elementary analysis for C$_{34}$H$_{39}$N$_3$O$_7$SCl$_2$:

|  | C | H | N |
|---|---|---|---|
| calculated (%) | 57.95 | 5.58 | 5.96 |
| found (%) | 57.81 | 5.33 | 5.92 |

(9) Synthesis of Boc-Tyr(Cl$_2$Bzl)-D-Cys(CH$_3$Bzl)-Gly-Phe-Cys(CH$_3$Bzl)-Arg(Tos)-CH$_3$Arg(Tos)-D-Leu-Arg(Tos)-NH$_2$ 983 mg of Boc-Tyr(Dl$_2$Bzl)-D-Cys(CH$_3$Bzl)-Gly-OH and 226 mg of N-hydroxybenzotriazole were dissolved in 5 ml of dimethylformamide. 316 mg of dicyclohexyl carbodiimide was added to the solution under cooling with ice. After stirring for 2 h, a solution of 1.94 g of CF$_3$COOH.H-Phe-Cys(CH$_3$Bzl)-Arg(Tos)-CH$_3$Arg(Tos)-D-Leu-Arg(Tos)-NH$_2$, synthesized by treating Boc-Phe-Cys(CH$_3$Bzl)-Arg(Tos)-CH$_3$Arg-(Tos)-D-Leu-Arg(Tos)-NH$_2$ with CF$_3$COOH in the presence of anisole, and 0.167 ml of N-methylmorpholine in 10 ml of dimethylformamide was added to the solution and the mixture was stirred in a refrigerator overnight. A precipitate thus formed was filtered. After silica gel column chromatography (eluted with MeOH/CHCl$_3$ =1/20) followed by solidification with methanol/ether, 2.0 g of Boc-Tyr(Cl$_2$ Bzl)-D-Cys(CH$_3$Bzl)-Gly-Phe-Cys(CH$_3$Bzl)-Arg-(Tos)-CH$_3$Arg(Tos)-D-Leu-Arg(Tos)-NH$_2$ was obtained.

m.p.: 123–130° C (dec)

TLC: Rf value 0.63 (methanol/chloroform, 1:27)

Optical rotation: [α]$_D$= −17.5° (C=1, dimethylformamide)

Elementary analysis for C$_{100}$H$_{129}$N$_{19}$O$_{18}$S$_5$Cl$_2$.C$_2$H$_5$OC$_2$H$_5$.3/2CH$_3$OH:

|  | C | H | N |
|---|---|---|---|
| calculated (%) | 56.60 | 6.52 | 11.89 |
| found (%) | 56.38 | 6.18 | 11.72 |

(10)

Synthesis of Tyr—D—Ċys—Gly—Phe—Ċys—Arg—CH$_3$Arg—D—Leu—Arg—NH$_2$ 515 mg of Boc-Tyr(Cl$_2$Bzl)-D-Cys(CH$_3$Bzl)-Gly-Phe-Cys(CH$_3$Blz)-Arg(Tos)-CH$_3$Arg(Tos)-D-Leu-Arg(Tos)-NH$_2$ was dissolved in 20 ml of HF in the presence of 2 ml of anisole at −5° C. in a closed hydrogen fluoride (HF) reaction device. The solution was stirred for 2 h and then HF was distilled out of the reaction system. The residue was washed with ether and dissolved in water. The solution was treated with Amberlite IRA-93 (acetic acid type) and then freeze-dried. 320 mg of the dried product was dissolved in 1.3 l of water and the solution was adjusted to pH with aqueous ammonia. Air was introduced therein under stirring for 2 days and the mixture was adjusted to pH 6 and then freeze-dried. The crude peptide thus obtained was purified according to high performance liquid chromatography [Nucleosil 5 C 18, 2 φ×25 cm, eluted with 0.05% HCl H$_2$O/CH$_3$CN, 88/12)] and freeze-dried to obtain 140 mg of Try—D—Ċys—Gly—Phe—Ċys—Arg—CH$_3$Arg—D—Leu—Arg—NH$_2$.

TLC: Rf value 0.56 (butanol/acetic acid/ pyridine/water, 15:5:5:8)

Optical rotation: [α]$_D$ = −29° C. =0.4, 0.01N-HCl)

M.S. (FAB): 1183 ([M+H]$^+$)

Amino acid analysis:

Gly 1.02(1); Cys 1.83(2); Leu 1.04(1);

Tyr 0.80(1); Phe 1.00(1); Arg 2.06(2);

(Peak due to CH$_3$Arg was not calculated)

EXAMPLES 3 to 29

Compounds shown in Table 1 were synthesized by the same conventional liquid phase process as in Examples 1 and 2. In these experiments, dynorphin derivatives modified in positions 1 to 3 (Tyr-Gly-Gly), in positions 4 to 7 (Phe-Leu-Arg-Arg), in positions 4 to 8 (Phe-Leu-Arg-Arg-Ile) and in positions 4 to 9 (Phe-Leu-Arg-Arg-Ile-Arg) were synthesized by the stepwise process starting from the C-terminal in each peptide. Then, the derivatives in positions 1 to 3 and those in positions 4 to 7, 4 to 8 or 4 to 9 were condensed together by the DCC-HOBt method or the mixed anhydride method. All the protective groups were removed with hydrogen fluoride (HF) and the product was purified according to preparative high-performance liquid chromatography using a reversed phase carrier. In Example 24, all the protective groups were removed with HF, and the compound was oxidized with air and then purified according to preparative high performance liquid chromatography. The reaction paths in the synthesis of the respective protected peptides are shown in Reaction Schemes 1 to 5.

The results of the determination of optical rotation $[\alpha]_D^{20}$, TLC Rf value and amino acid analysis of the intended peptides obtained as above are shown in Table 6.

TABLE 5

| Example | Compound |
|---|---|
| 3 | $CH_3Tyr$—Gly—Gly—Phe—Leu—Arg—Arg—$NH_2$ |
| 4 | $CH_3Tyr$—Gly—Gly—Phe—Leu—Arg—Arg—$NHCH_2CH(CH_3)CH_2CH_3$ |
| 5 | $CH_3Tyr$—Gly—Gly—Phe—Leu—Arg—Arg—D—Leu—OH |
| 6 | $CH_3Tyr$—Gly—Gly—Phe—Leu—Arg—Arg—D—Leu—$OC_2H_5$ |
| 7 | $CH_3Tyr$—Gly—Gly—Phe—Leu—Arg—Arg—D—Leu—$NH_2$ |
| 8 | $CH_3Tyr$—Gly—Gly—Phe—Leu—Arg—Arg—D—Leu—$NHC_2H_5$ |
| 9 | $CH_3Tyr$—Gly—Gly—Phe—Leu—Arg—Arg—D—Leu—$NH(CH_2)_5CH_3$ |
| 10 | $CH_3Tyr$—Gly—Gly—Phe(p-$NO_2$)—Leu—Arg—Arg—D—Leu—$NH_2$ |
| 11 | $CH_3Tyr$—Gly—Gly—Phe—Leu—homoArg—Arg—D—Leu—$NH_2$ |
| 12 | $CH_3Tyr$—D—Ala—Gly—Phe—Leu—Arg—Arg—D—Leu—$NH_2$ |
| 13 | $CH_3Tyr$—Gly—Gly—$CH_3$Phe—Leu—Arg—Arg—D—Leu—$NH_2$ |
| 14 | $CH_3Tyr$—Gly—Gly—Phe—$CH_3$Leu—Arg—Arg—D—Leu—$NH_2$ |
| 15 | $CH_3Tyr$—Gly—Gly—D—Phe—Leu—Arg—Arg—D—Leu—$NH_2$ |
| 16 | Tyr—D—Ala—Gly—Phe—Leu—Arg—Arg—D—Leu—$NH_2$ |
| 17 | Tyr—Sar—Gly—Phe—Leu—Arg—Arg—D—Leu—$NH_2$ |
| 18 | $CH_3Tyr$—Gly—Gly—Phe—Leu—$CH_3$Arg—Arg—D—Leu—$NH_2$ |
| 19 | $CH_3Tyr$—Gly—Gly—Phe—Leu—Arg—$CH_3$Arg—D—Leu—$NH_2$ |
| 20 | $CH_3Tyr$—Gly—Gly—Phe—tert-Leu—Arg—$CH_3$Arg—D—Leu—$NHC_2H_5$ |
| 21 | $CH_3Tyr$—Gly—Gly—Phe(p-$NO_2$)—Leu—Arg—$CH_3$Arg—D—Leu—$NHC_2H_5$ |
| 22 | $CH_3Tyr$—Gly—Gly—Phe—Leu—Lys—$CH_3$Arg—D—Leu—$NH_2$ |
| 23 | Tyr—D—Ser—Gly—Phe—Ser—Arg—$CH_3$Arg—D—Leu—$NHC_2H_5$ |
| 24 | 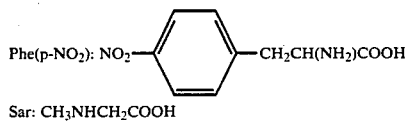<br>Tyr—D—Cys—Gly—Phe—Cys—Arg—$CH_3$Arg—D—Leu—$NHC_2H_5$ |
| 25 | $CH_3Tyr$—Gly—Gly—Phe—Leu—Arg—Arg—D—Leu—Arg—$NH_2$ |
| 26 | $CH_3Tyr$—Gly—Gly—Phe—Leu—Arg—Arg—D—Glu—Arg—$NH_2$ |
| 27 | $CH_3Tyr$—Gly—Gly—Phe—Leu—Arg—$CH_3$Arg—D—Leu—Arg—$NHC_2H_5$ |
| 28 | $CH_3Tyr$—Gly—Gly—Phe(p-$NO_2$)—Leu—Arg—$CH_3$Arg—D—Leu—Arg—$NHC_2H_5$ |
| 29 | $CH_3Tyr$—Gly—Gly—Phe—Met(O)—Arg—$CH_3$Arg—D—Leu—Arg—$NH_2$ | tert-Leu: $(CH_3)_3CCH(NH_2)COOH$
homoArg: $NH_2C(=NH)NHCH_2CH_2CH_2CH_2CH(NH_2)COOH$ Phe(p-$NO_2$): $NO_2$—⟨⟩—$CH_2CH(NH_2)COOH$ Sar: $CH_3NHCH_2COOH$ Reaction Scheme 1
Examples 3 and 4

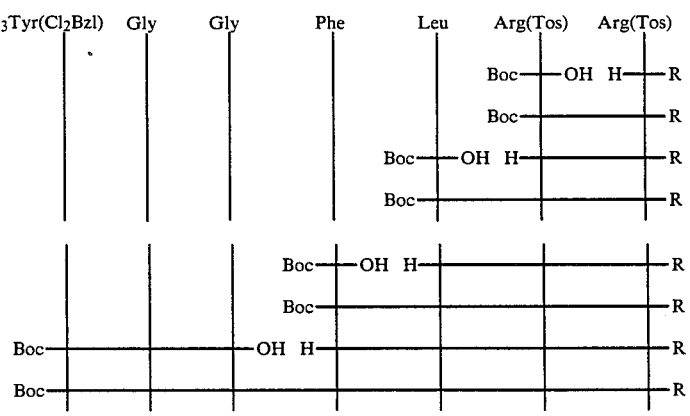

R: $NH_2$, $NHCH_2CH(CH_3)CH_2CH_3$

Reaction Scheme 2
Examples 5 to 18

| A | B | Gly | C | D | E | Arg(Tos) | D—Leu |
|---|---|---|---|---|---|---|---|
| | | | | | | Boc——OH H— | —R |
| | | | | | | Boc— | —R |
| | | | | | Boc——OH H— | | —R |
| | | | | | Boc— | | —R |
| | | | | Boc——OH H— | | | —R |
| | | | | Boc— | | | —R |
| | | | Boc——OH H— | | | | —R |
| | | Boc— | | | | | —R |
| Boc— | | —OH H— | | | | | —R |
| Boc— | | | | | | | —R |

A: Tyr(Cl₂Bzl),CH₃Tyr(Cl₂Bzl),
B: Gly,D—Ala,Sar.
C: phe,D—Phe, CH₃Phe,Phe(p-NO₂).
D: Leu,CH₃Leu.
E: Arg(Tos),homoArg(Tos).
R: OBzl,OC₂H₅,NH₂,NHC₂H₅,NH(CH₂)₅CH₃

(In Examples 11 and 18, Z-homoArg (Tos) OH and Z-CH₃Arg(Tos)OH, respectively, were used as the protected amino acid E.)

Reaction Scheme 3
Examples 19 to 24

| A | B | Gly | C | D | E | CH₃Arg(Tos) | D—Leu |
|---|---|---|---|---|---|---|---|
| | | | | | | Z——OH H— | —R |
| | | | | | | Z— | —R |
| | | | | | Boc——OH H— | | —R |
| | | | | | Boc— | | —R |
| | | | | Boc——OH H— | | | —R |
| | | | | Boc— | | | —R |
| | | | Boc——OH H— | | | | —R |
| | | Boc— | | | | | —R |
| Boc— | | —OH H— | | | | | —R |
| Boc— | | | | | | | —R |

A: Tyr(Cl₂Bzl),CH₃Tyr(Cl₂Bzl).
B: Gly,D-Ser(Bzl),D-Cys(CH₃Bzl).
C: Phe,Phe(p-NO₂).
D: Leu,tert-Leu,Ser(Bzl),Cys(CH₃Bzl).
E: Arg(Tos),Lys(Z).
R: NH₂,NHC₂H₅

Reaction Scheme 4
Examples 25 and 26
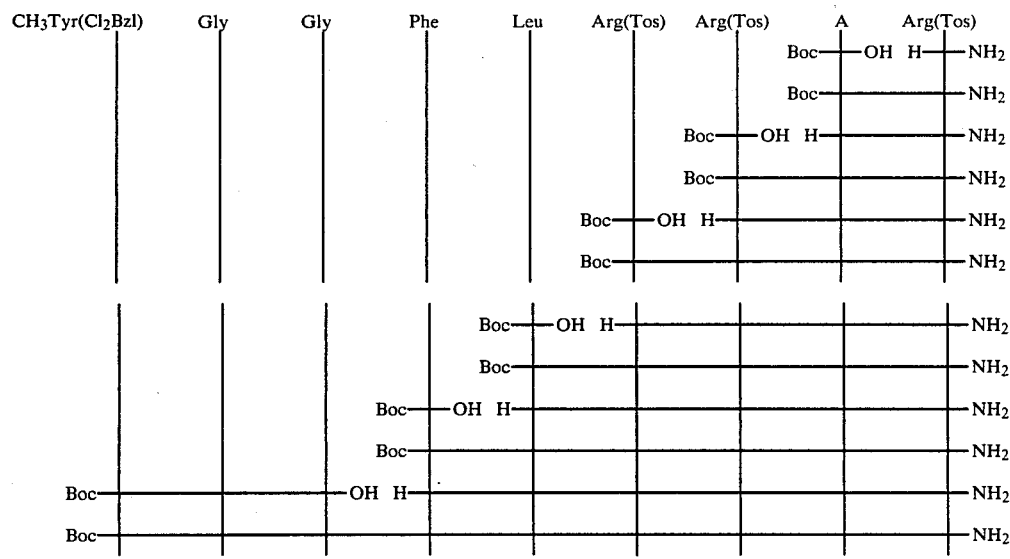
A: D-Leu, D-Glu(OBzl)
Reaction Scheme 5
Examples 27 to 29
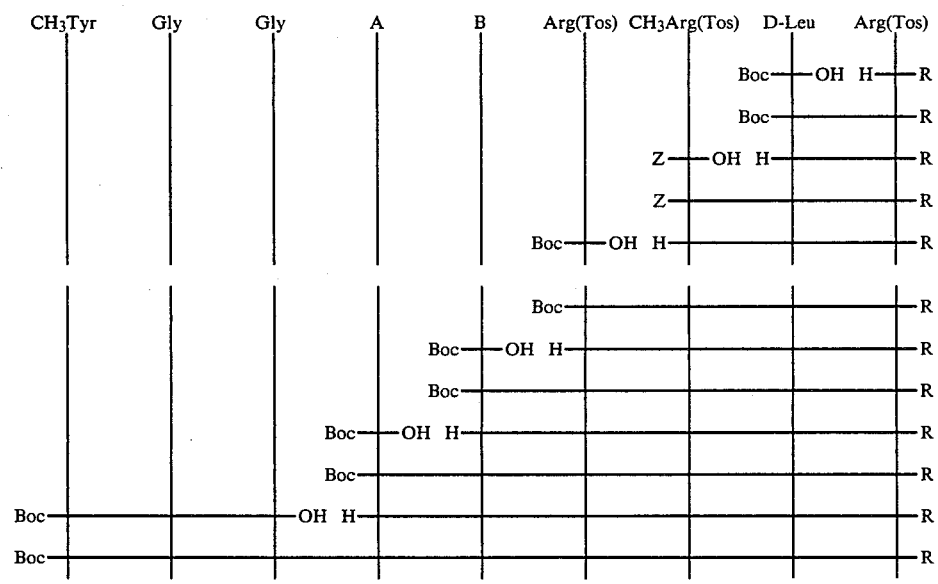
A: Phe, Phe(p-NO$_2$). B: Leu, Met(O). R: NH$_2$, NHC$_2$H$_5$
TABLE 6
| Example | $[\alpha]_D^{20}$ | TLC Rf value | Amino acid analysis |
|---|---|---|---|
| 3 | −6.7° | 0.53 | Gly 1.97, Leu 1.03, Phe 1.00, Arg 2.30 |
| 4 | −12.1° | 0.62 | Gly 1.96, Leu 1.00, Phe 1.00, Arg 2.01 |
| 5 | −1.8° | 0.65 | Gly 2.01, Leu 2.00, Phe 1.00, Arg 1.99 |
| 6 | +0.8° | 0.63 | Gly 1.94, Leu 1.96, Phe 1.00, Arg 1.97 |
| 7 | −7.5° | 0.62 | Gly 1.95, Leu 1.96, Phe 1.00, Arg 1.97 |
| 8 | +5.0° | 0.64 | Gly 1.91, Leu 2.14, Phe 1.00, Arg 2.18 |
| 9 | +1.0° | 0.68 | Gly 1.92, Leu 1.95, Phe 1.00, Arg 1.95 |
| 10 | +3.4° | 0.59 | Gly 1.97, Leu 2.00, Arg 2.01 |
| 11 | −4.2° | 0.61 | Gly 1.95, Leu 1.96, Phe 1.00, Arg 1.01 |
| 12 | +13.9° | 0.68 | Gly 1.01, Leu 1.96, Phe 1.00, Arg 1.98, Ala 1.00 |
| 13 | −17.2° | 0.68 | Gly 1.92, Leu 2.00, Arg 2.03 |

TABLE 6-continued

| Example | $[\alpha]_D^{20}$ | TLC Rf value | Amino acid analysis |
|---|---|---|---|
| 14 | −11.5° | 0.61 | Gly 1.99, Leu 1.02, Phe 1.00, Arg 2.03 |
| 15 | −12.0° | 0.67 | Gly 1.90, Leu 1.93, Phe 1.00, Arg 1.94 |
| 16 | +15.0° | 0.69 | Gly 1.07, Leu 1.97, Phe 1.00, Arg 1.99, Ala 1.03, Tyr 0.95 |
| 17 | −3.8° | 0.64 | Gly 1.00, Leu 1.98, Phe 1.00, Arg 2.00, Tyr 0.89 |
| 18 | −19.7° | 0.59 | Gly 1.93, Leu 1.91, Phe 1.00, Arg 0.98 |
| 19 | −23.4° | 0.62 | Gly 1.92, Leu 1.95, Phe 1.00, Arg 0.99 |
| 20 | −19.1° | 0.70 | Gly 2.06, Leu 1.01, Phe 1.00, Arg 0.99 |
| 21 | −16.6° | 0.69 | Gly 1.99, Leu 2.00, Arg 0.99 |
| 22 | −23.3° | 0.62 | Gly 1.97, Leu 1.99, Phe 1.00, Lys 1.03 |
| 23 | −4.8° | 0.65 | Gly 1.01, Leu 1.00, Phe 1.00, Arg 1.01, Ser 1.72, Tyr 1.00 |
| 24 | −29.1° | 0.70 | Gly 1.01, Leu 1.05, Phe 1.00, Arg 1.02, Tyr 0.82, Cys 1.89 |
| 25 | −7.8° | 0.64 | Gly 2.03, Leu 2.08, Phe 1.00, Arg 3.22 |
| 26 | −6.1° | 0.43 | Gly 1.93, Leu 0.98, Phe 1.00, Arg 2.95, Glu 0.98 |
| 27 | −31.8° | 0.62 | Gly 1.94, Leu 1.90, Phe 1.00, Arg 1.91 |
| 28 | −27.2° | 0.52 | Gly 1.96, Leu 2.00, Arg 2.03 |
| 29 | −23.0° | 0.46 | Gly 2.00, Leu 1.00, Phe 1.00, Arg 1.97 |

In the amino acid analysis, the proportions of only the amino acids of Gly, Leu, Phe, Arg, Ala, Tyr, Lys, Ser, Cys and Glu were calculated.
$[\alpha]_D^{20}$ determination; C = 0.4 0.01N—HCl
TLC.Rf value determination; butanol/acetic acid/pyridine/water = 15:5:5:8

EXAMPLE 30

Synthesis of CH$_3$-Tyr-Gly-Gly-Phe-Leu-Arg-CH$_3$Arg-D-Ala-OH:

(1) Synthesis of Z-CH$_3$Arg(Tos)-D-Ala-OBu$^t$ 3.336 g of Z-CH$_3$Arg(Tos)OH was dissolved in 20 ml of tetrahydrofuran. The solution was cooled to −30° C. 0.77 ml of N-methylmorpholine and 0.669 ml of ethyl chlorocarbonate were added to the solution. After 5 min, a solution of 1.272 g of HCl·H-D-Ala-OBu$^t$ and 1.16 ml of N-methylmorpholine in 20 ml of tetrahydrofuran was added thereto and the mixture was stirred at about −5° C. for 2 h. After concentration, the residue was dissolved in ethyl acetate and washed with an aqueous NaHCO$_3$ solution and water, successively. After concentration to dryness, 4.16 g of glassy Z-CH$_3$Arg-(Tos)-D-Ala-OBu$^t$ was obtained.

TLC: Rf value 0.69 (methanol/chloroform, 1:7)
Optical rotation: $[\alpha]_D = -15.5°$ (C=1, methanol)
Elementary analysis for C$_{29}$H$_{41}$N$_5$O$_7$S:

|  | C | H | N |
|---|---|---|---|
| calculated (%) | 57.70 | 6.85 | 11.60 |
| found (%) | 57.74 | 6.59 | 11.31 |

(2) SYnthesis of Z-Arg(Tos)-CH$_3$Arg(Tos)-D-Ala-OBu$^t$ 2.87 g of CH$_3$Arg(Tos)-D-AlaOBu$^t$, obtained by catalytic reduction of Z-CH$_3$Arg(Tos)-D-Ala-OBu$^t$ in the presence of Pd-C, 3.392 g of Z-Arg(Tos)-OH and 1.188 g of N-hydroxybenzotriazole were dissolved in 10 ml of dimethyl formamide. 1.662 g of dicyclohexylcarbodiimide was added to the solution under cooling with ice and the mixture was stirred in a refrigerator for two days. The precipitate thus formed was filtered out and the filtrate was concentrated. The residue was purified according to silica gel column chromatography (eluent: methanol/chloroform=1/20) to obtain 2.04 g of glassy Z-Arg(Tos)-CH$_3$Arg(Tos)-D-Ala-OBu$^t$.

TLC: Rf value 0.57 (methanol/chloroform, 1.7)
Optical rotation: $[\alpha]_D = -31.6°$ (C=;, methanol)
Elementary analysis for C$_{42}$H$_{59}$N$_9$O$_{10}$S$_2$·1/2H$_2$O

|  | C | H | N |
|---|---|---|---|
| calculated (%) | 54.65 | 6.62 | 13.66 |
| found (%) | 54.64 | 6.48 | 13.72 |

(3) Synthesis of Z-Leu-Arg(Tos)-CH$_3$Arg(Tos)-D-Ala-OBU$^t$ 0.629 g of Z-Leu-OH was dissolved in 15 ml of dimethylformamide. The solution was cooled to −20° C. 0.261 ml of N-methylmorpholine and 0.277 ml of ethyl chlorocarbonate were added to the solution. After 5 min, a solution of 1.76 g of HCl.H-Arg(Tos)-CH$_3$Arg-(Tos)-D-Ala-OBu$^t$, prepared by catalytic reduction of Z-Arg(Tos)-CH$_3$Arg(Tos)-D-Ala-OBu$^t$ in the presence of Pd-C, and 0.356 ml of N-methylmorpholine in 15 ml of dimethylformamide was added to the solution and the mixture was stirred at about −5° C. for 2 h. After concentration, the residue was dissolved in ethyl acetate and the solution was washed with an aqueous NaHCO$_3$ solution and water, successively. After concentration to dryness, 2.11 g of glassy Z-Leu-Arg(Tos)-CH$_3$Arg-(Tos)-D-Ala-OBu$^t$ was obtained.

TLC: Rf value 0.57 (methanol/chloroform, 1:7)
Optical rotation: $[\alpha]_D = -36.2°$ (C=1, methanol)
Elementary analysis for C$_{48}$H$_{70}$N$_{10}$O$_{11}$S$_2$·½CH$_3$COOC$_2$H$_5$:

|  | C | H | N |
|---|---|---|---|
| calculated (%) | 56.06 | 6.96 | 13.07 |
| found (%) | 56.02 | 6.85 | 13.08 |

(4) Synthesis of Z-Phe-Leu-Arg(Tos)-CH$_3$Arg(Tos)-D-Ala-OBu$^t$ 595 mg of Z-Phe-OH was dissolved in 15 ml of dimethylformamide. The solution was cooled to −20° C. 0.219 ml of N-methylmorpholine and 0.190 ml of ethyl chlorocarbonate were added to the solution. After 5 min, a solution of 1.68 g of HCl.H-Leu-Arg(Tos)-CH$_3$Arg(Tos)-D-Ala-OBut, prepared by catalytic reduction of Z-Leu-Arg(Tos)-CH$_3$Arg-(Tos)-D-Ala-OBu$^t$ in the presence of Pd-C, and 0.299 ml of N-methylmorpholine in 15 ml of dimethylformamide was added to the solution and the mixture was stirred at about $-5°$ C. for 2 h. After concentration, the residue was dissolved in ethyl acetate and the solution was washed with an aqueous $NaHCO_3$ solution and water, successively. The solvent was distilled off and ether was added to the residue. After decantation followed by concentration to dryness, 1.87 g of glassy Z-Phe-Leu-Arg(Tos)$CH_3$Arg(Tos)-D-Ala-OBu$^t$ was obtained.

TLC: Rf value 0.61 (methanol/chloroform, 1:7) optical rotation: $[\alpha]_D = -34.7°$ (C=1, methanol)

Elementary analysis for $C_{57}H_{79}N_{11}O_{12}S_2 \cdot C_2H_5OC_2H_5$:

|  | C | H | N |
| --- | --- | --- | --- |
| calculated (%) | 58.68 | 7.19 | 12.34 |
| found (%) | 58.66 | 6.83 | 12.42 |

(5) Synthesis of Boc-$CH_3$Tyr($Cl_2$Bzl)-Gly-Gly-Phe-Leu-Arg(Tos)-$CH_3$Arg(Tos)-D-Ala-OBu$^t$ 969 mg of Boc-$CH_3$Tyr($Cl_2$Bzl)-Gly-Gly-OH was dissolved in 12 ml of dimethylformamide. The solution was cooled to $-20°$ C. 0.188 ml of N-methylmorpholine and 0.163 ml of ethyl chlorocarbonate were added to the solution. After 5 min, a solution of 1.67 g of HCl.H-Phe-Leu-Arg(Tos)-$CH_3$Arg(Tos)-D-Ala-OBu$^t$, prepared by catalytic reduction of Z-Phe-Leu-Arg(Tos)-$CH_3$Arg(Tos)-D-Ala-OBu$^t$ in the presence of PD-C, and 0.256 ml of N-methylmorpholine in 15 ml of dimethylformamide was added to the solution and the mixture was stirred at about $-5°$ C. for 2 h. After concentration, the residue was dissolved in ethyl acetate and the solution was washed with an aqueous $NaHCO_3$ solution and water, successively. The solvent was distilled off under reduced pressure and the residue was solidified with methanol/ether to obtain 2.196 g of Boc-$CH_3$Tyr($Cl_2$Bzl)-Gly-Gly-Phe-Leu-Arg(Tos)-$CH_3$Arg(Tos)-D-Ala-OBu$^t$.

m.p.: 130–135° C. (dec)

TLC: Rf value 0.61 (methanol/chloroform, 1:7)

Optical rotation: $[\alpha]_D = 40.7°$ (C=1, methanol)

Elementary analysis for $C_{75}H_{102}N_{14}O_{16}S_2Cl_2 \cdot 2CH_3OH$:

|  | C | H | N |
| --- | --- | --- | --- |
| calculated (%) | 55.89 | 6.70 | 11.85 |
| found (%) | 55.95 | 6.42 | 11.78 |

(6) Synthesis of $CH_3$Tyr-Gly-Gly-Phe-Leu-Arg-$CH_3$Arg-D-Ala-OH 200 mg of Boc-$CH_3$Tyr($Cl_2$Bzl)-Gly-Gly-Phe-Leu-Arg(Tos)-$CH_3$Arg(Tos)-D-Ala-OBu$^t$ was dissolved in 10 ml of HF at $-5°$ C. in the presence of 0.2 ml of anisole in a closed hydrogen fluoride (HF) reaction device. The solution was stirred for 1 h and HF was distilled off from the reaction system. The residue was washed with ether and then dissolved in water. The solution was treated with Amberlite IRA-93 (acetic acid type) and then freeze-dried. 120 mg of the crude peptide thus obtained was purified according to high performance liquid chromatography [Nucleosil 5 C 18, $2\phi \times 25$ cm, eluted with 0.05 % HCl ($H_2O/CH_3CN$, 92:8)] and freeze-dried to obtain 60 mg of $CH_3$Tyr-Gly-Gly-Phe-Leu-Arg-$CH_3$Arg-D-Ala-OH.

TLC: Rf value 0.54 (butanol/acetic acid/pyridine/water, 15:5:5:8)

Optical rotation: $[\alpha]_D = -35.1°$ (C=0.4, 0.01N-HCl)

M.S. (FAB): 967 ([M+H]$^+$)

Amino acid analysis:

Gly 1.95(2); Leu 1.00(1); Phe 1.00(1);

Arg 0.99(1); Ala 1.01(1).

(Peaks due to $CH_3$Tyr and $CH_3$Arg not calculated)

EXAMPLE 31

Synthesis of $CH_3$Tyr-Gly-Gly-Phe-Leu-Arg-$CH_3$Arg-$CH_3$Ala-OH (1) Synthesis of Z-$CH_3$Arg(Tos)-$CH_3$Ala-OBu$^t$ 4.508 g of Z-$CH_3$Arg(Tos)OH, 1.683 g of HCl.-$CH_3$Ala-OBu$^t$, 1.533 g of N-hydroxybenzotriazole and 1.04 ml of N-methylmorpholine were dissolved in 10 ml of dimethylformamide. 2.144 g of dicyclohexylcarbodiimide was added to the solution under cooling with ice and the mixture was stirred in a refrigerator overnight. The precipitate thus formed was filtered off and the filtrate was concentrated. The residue was dissolved in ethyl acetate and the solution was washed with an aqueous citric acid solution, aqueous $NaHCO_3$ solution and water, successively. After concentration to dryness, 4.24 g of glassy Z-$CH_3$-Arg(Tos)-$CH_3$Ala-OBu$^t$ was obtained.

TLC: Rf value 0.61 (methanol/chloroform, 1:7)

Optical rotation: $[\alpha]_D = -57.8°$ (C=1, methanol)

Elementary analysis for $C_{30}H_{43}N_5O_7S$:

|  | C | H | N |
| --- | --- | --- | --- |
| calculated (%) | 58.33 | 7.02 | 11.33 |
| found (%) | 58.11 | 6.88 | 11.41 |

(2) Synthesis of Z-Arg(Tos)-$CH_3$Arq(Tos)-$CH_3$Ala-OBu$^t$ 2.90 g of $CH_3$Arg(Tos)-$CH_3$Ala-OBu$^t$, obtained by catalytic reduction of Z-$CH_3$Arg(Tos)-$CH_3$Ala-OBu$^t$ in the presence of Pd-C, 3,329 g of Z-Arg(Tos)OH and 1.166 g of N-hydroxybenzotriazole were dissolved in 10 ml of dimethylformamide. 1.359 g of dicyclohexylcarbodiimide was added to the solution under cooling with ice and the mixture was stirred in a refrigerator for two days. The precipitate thus formed was filtered off and the filtrate was concentrated. The residue was purified according to silica gel column chromarography (eluent: $MeOH/CHCl_3 = 1/15$) to obtain 2.1 g of glassy Z-Arg(Tos)-$CH_3$Arg(Tos)-$CH_3$Ala-OBu$^t$.

TLC: Rf value 0.46 (methanol/chloroform, 1:7) optical rotating: $[\alpha]_D = -57.1°$ (C=1, methanol)

Elementary analysis for $C_{43}H_{61}N_9O_{10}S_2 \cdot 3/2H_2O$:

|  | C | H | N |
| --- | --- | --- | --- |
| calculated (%) | 54.07 | 6.75 | 13.20 |
| found (%) | 54.10 | 6.35 | 13.18 |

(3) Synthesis of Z-Leu-Arg(Tos)-$CH_3$Arg(Tos)-$CH_3$Ala-OBu$^t$ 247 g of Z-Leu-OH was dissolved in 10 ml of dimethylformamide. The solution was cooled to $-20°$ C. 0.102 ml of N-methylmorpholine and 0.089 ml of ethyl chlorocarbonate were added to the solution. After 5 min, a solution of 700 mg of HCl.H-Arg(Tos)-$CH_3$Arg(Tos)-

CH$_3$Ala-OBu$^t$, obtained by catalytic reduction of Z-Arg(Tos)-CH$_3$Arg(Tos)-CH$_3$Ala-OBu$^t$ in the presence of Pd-C, and 0.139 ml of N-methylmorpholine in 10 ml of dimethylformamide was added to the solution and the mixture was stirred at about $-5°$ C. for 2 h. After concentration, the residue was dissolved in ethyl acetate and the solution was washed with an aqueous NaHCO$_3$ solution and water, successively. The solvent was distilled off and ether was added to the residue. After decantation followed by concentration to dryness, 0.86 g of glassy Z-Leu-Arg(Tos)-CH$_3$Arg(Tos)-CH$_3$Ala-OBu$^t$ was obtained TLC: Rf value 0.48 (methanol/chloroform, 1:7)
Optical rotation: $[\alpha]_D = -60.3°$ (C=1, methanol)
Elementary analysis for C$_{49}$H$_{72}$N$_{10}$O$_{11}$S$_2$·C$_2$H$_5$OC$_2$H$_5$:

|  | C | H | N |
|---|---|---|---|
| calculated (%) | 57.07 | 7.41 | 12.55 |
| found (%) | 56.83 | 7.02 | 12.64 |

(4) Synthesis of
Z-Phe-Leu-Arg(Tos)-CH$_3$Arg(Tos)-CH$_3$Ala-OBu$^t$ 224 mg of Z-Phe-OH was dissolved in 7 ml of dimethylformamide. The solution was cooled to $-20°$ C. 0.082 ml of N-methylmorpholine and 0.071 ml of ethyl chlorocarbonate were added to the solution. After 5 min, a solution of 640 mg of HCl·H-Leu-Arg(Tos)-CH$_3$Arg(Tos)-CH$_3$Ala-OBu$^t$, prepared by catalytic reduction of Z-Leu-Arg(Tos)-CH$_3$Arg(Tos)-CH$_3$Ala-OBu$^t$ in the presence of Pd-C, and 0.112 ml of N-methylmorpholine in 7 ml of dimethylformamide was added to the solution and the mixture was stirred at about $-5°$ C. for 2 h. After concentration, the residue was dissolved in ethyl acetate and the solution was washed with an aqueous NaHCO$_3$ solution and water, successively. The solvent was distilled off and ether was added to the residue. After decantation followed by concentration to dryness, 770 mg of glassy Z-Phe-Leu-Arg(Tos) CH$_3$Arg(Tos)-CH$_3$Ala-OBu$^t$ was obtained TLC: Rf value 0.54 (methanol/chloroform, 1:7)
Optical rotation: $[\alpha]_D = -59.6°$ (C=1, methanol)
Elementary analysis for C$_{58}$H$_{81}$N$_{11}$O$_{12}$S$_2$·C$_2$H$_5$OC$_2$H$_5$:

|  | C | H | N |
|---|---|---|---|
| calculated (%) | 58.98 | 7.26 | 12.20 |
| found (%) | 58.68 | 6.91 | 12.24 |

(5) Synthesis of
Boc-CH$_3$-Tyr(Cl$_2$Bzl)-Gly-Gly-Phe-Leu-Arg(Tos)-CH$_3$Arg(Tos)-CH$_3$Ala-OBu$^t$ 350 mg of Boc-CH$_3$Tyr(Cl$_2$Bzl)-Gly-Gly-OH was dissolved in 5 ml of dimethylformamide. The solution was cooled to $-20°$ C. 0.068 ml of N-methylmorpholine and 0.059 ml of ethyl chlorocarbonate were added to the solution. After 5 min, a solution of 610 mg of HCl·H-Phe-Leu-Arg(Tos)-CH$_3$Arg(Tos)-CH$_3$Ala-OBu$^t$, prepared by catalytic reduction of Z-Phe-Leu-Arg(Tos)-CH$_3$Arg(Tos)-CH$_3$Ala-OBu$^t$ in the presence of Pd-C, and 0.092 ml of N-methylmorpholine in 6 ml of dimethylformamide was added to the solution and the mixture was stirred at about $-5°$ C. for 2 h. After concentration, the residue was dissolved in ethyl acetate and the solution was washed with an aqueous NaHCO$_3$ solution and water, successively. After concentration followed by solidification with methanol/ether, 760 mg of Boc-CH$_3$Tyr(Cl$_2$Bzl)-Gly-Gly-Phe-Leu-Arg(Tos)-CH$_3$Arg(Tos)-CH$_3$Ala-OBu$^t$ was obtained.

m.p.: 125-133° C. (dec)
TLC: Rf value 0.55 (methanol/chloroform, 1:7)
Optical rotation: $[\alpha]_D = -56.4°$ C. (C=1, methanol)
Elementary analysis for C$_{76}$H$_{104}$N$_{14}$O$_{16}$S$_2$Cl$_2$·½C$_2$H$_5$OC$_2$H$_5$:

|  | C | H | N |
|---|---|---|---|
| calculated (%) | 57.06 | 6.69 | 11.94 |
| found (%) | 56.71 | 6.46 | 11.49 |

6) Synthesis of
CH$_3$Tyr-Gly-Gly-Phe-Leu-Arg-CH$_3$Arg-CH$_3$Ala-OH 210 ml of Boc-CH$_3$Tyr(Cl$_2$Bzl)-Gly-Gly-Phe-Leu-Arg(Tos)-CH$_3$Arg(Tos)-CH$_3$Ala-OBu$^t$ was dissolved in 10 ml of HF at $-5°$ C. in the presence of 0.2 ml of anisole in the HF reaction device of a closed system. The solution was stirred for 1 h and then HF was distilled off from the reaction system. The residue was washed with ether and dissolved in water. The solution was treated with Amberlite IRA-93 (acetic acid type) and then freeze-dried. 130 mg of the crude peptide thus obtained was purified according to high performance liquid chromatography [Nucleosil 5 C 18, 2 φ×25 cm, eluted with 0.05 % HCl (H$_2$O/CH$_3$CN, 91:9)] and freeze-eluted dried to obtain 50 mg of CH$_3$Tyr-Gly-Gly-Phe-Leu-Arg-CH$_3$Arg-CH$_3$Ala-OH.

TLC: Rf value 0.54 (butanol/acetic acid/pyridine/water, 15:5:5:8)
Optical rotation: $[\alpha]_D^{20} = -64.7°$ (C=0.4, 0.01N-HCl)
M.S. (FAB): 981 ([M+H]$^+$)
Amino acid analysis:
Gly 1.92(2); Leu 1.04(1); Phe 1.00(1);
Arg 0.986 (1).
(Peaks due to CH$_3$Tyr, CH$_3$Arg and CH$_3$Ala not calculated)

EXAMPLE 32 to 41

Compounds shown in Table 7 were synthesized by the same conventional liquid phase process as in Examples 30 and 31. In these experiments, dynorphin derivatives modified in positions 1 to 3 (Tyr-Gly-Gly), in positions 4 to 8 (Phe-Leu-Arg-Arg-Ile), in positions 4 to 9 (Phe-Leu-Arg-Arg-Ile-Arg) and in positions 4 to 10 (Phe-Leu-Arg-Arg-Ile-Arg-Pro) were synthesized by the stepwise process starting from the C-terminal in each peptide. Then, the derivatives in positions 1 to 3 and those in positions 4 to 8, 4 to 9 or 4 to 10 were condensed together by DCC-HOBt method or mixed acid anhydride method. All the protective groups were removed with hydrogen fluoride (HF) and the product was purified according to preparative high-performance liquid chromatography using a reversed phase carrier.

The results of the determination of optical rotation $[\alpha]_D^{20}$, TLC Rf value and amino acid analysis of the intended peptides obtained as above are shown in Table 8.

TABLE 7

| Example | Compound |
|---|---|
| 32 | CH₃Tyr—Gly—Gly—Phe—Leu—Arg—CH₃Arg—Ile—OH |
| 33 | CH₃Tyr—Gly—Gly—Phe—Leu—Arg—CH₃Arg—Asp—OH |
| 34 | CH₃Tyr—Gly—Gly—Phe—Leu—Arg—CH₃Arg—D—Leu—OH |
| 35 | CH₃Tyr—Gly—Gly—Phe—Leu—Arg—CH₃Arg—D—Glu—OH |
| 36 | CH₃Tyr—Gly—Gly—Phe—Leu—Arg—CH₃Arg—CH₃Ile—OH |
| 37 | CH₃Tyr—Gly—Gly—Phe—Leu—Arg—CH₃Arg—Sar—OH |
| 38 | CH₃Tyr—Gly—Gly—Phe—Leu—Arg—CH₃Arg—β-Ala—OH |
| 39 | CH₃Tyr—Gly—Gly—Phe—Leu—Arg—CH₃Arg—D-Leu—Asp—OH |
| 40 | CH₃Tyr—Gly—Gly—Phe—Leu—Arg—CH₃Arg—D-Leu—Phe—OH |
| 41 | CH₃Tyr—Gly—Gly—Phe—Leu—Arg—CH₃Arg—D-Leu—Arg—D-Glu—OH |

Reaction Scheme 6
Examples 32 to 38

R: Ile, Asp(OBuᵗ), D-Leu, D-Glu(OBuᵗ), CH₃Ile, Sar, β-Ala

Reaction Scheme 7
Examples 39 and 40

-continued
Reaction Scheme 7
Examples 39 and 40

R: Asp(OBu'), Phe

Reaction Scheme 8
Example 41

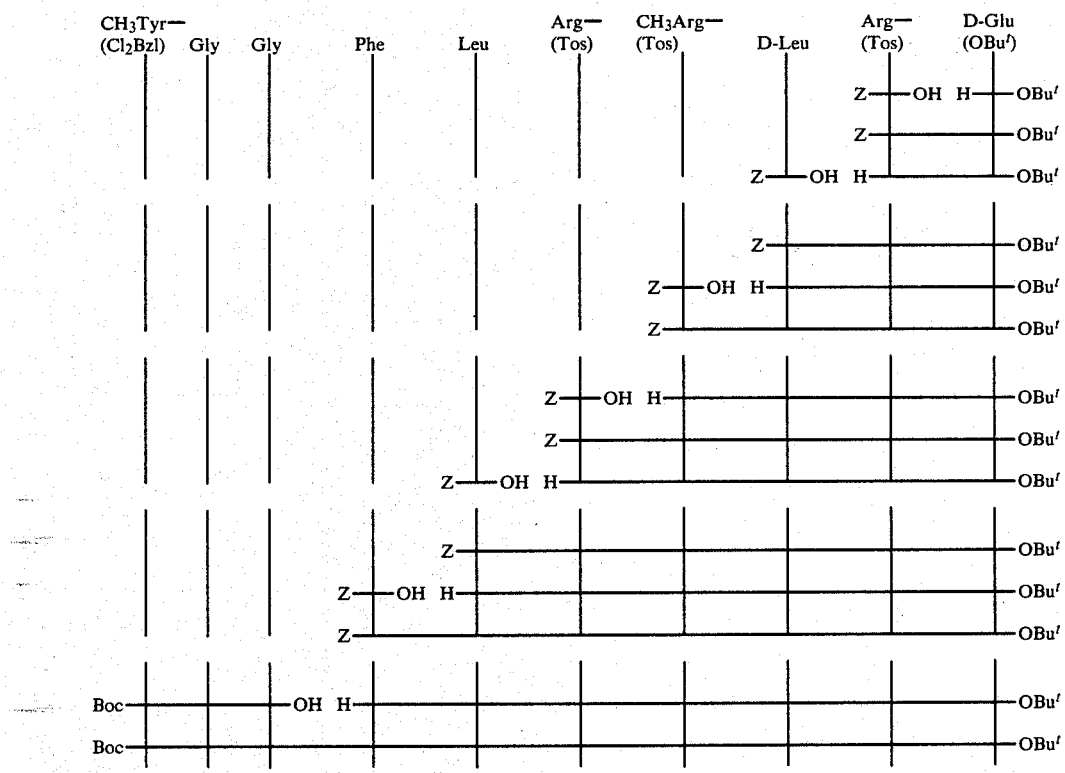

TABLE 8

| Example | $[\alpha]_D^{20}$ | TLC Rf value | Amino acid analysis |
|---|---|---|---|
| 32 | −10.6 | 0.63 | Gly 1.96, Leu 1.05, Phe 1.00, Arg 1.01, Ile 0.99 |
| 33 | −35.4 | 0.48 | Gly 1.96, Leu 0.99, Phe 1.00, Arg 0.99, Asp 1.01 |
| 34 | −32.4 | 0.68 | Gly 1.95, Leu 1.95, Phe 1.00, Arg 0.99 |
| 35 | −30.8 | 0.51 | Gly 1.93, Leu 1.00, Phe 1.00, Arg 1.00, Glu 1.01 |
| 36 | −67.1 | 0.63 | Gly 1.95, Leu 0.97, Phe 1.00, Arg 0.96 |
| 37 | −23.9 | 0.51 | Gly 1.97, Leu 1.01, Phe 1.00, Arg 1.00 |
| 38 | −29.2 | 0.56 | Gly 1.96, Leu 1.01, Phe 1.00, Arg 1.01 |
| 39 | −28.6 | 0.58 | Gly 1.96, Leu 1.98, Phe 1.00, Arg 1.00, Asp 1.06 |
| 40 | −25.0 | 0.70 | Gly 1.93, Leu 2.01, Phe 2.00, Arg 0.96 |
| 41 | −30.8 | 0.51 | Gly 1.96, Leu 1.97, Phe 1.00, Arg 1.99, Glu 1.01 |

In the amino acid analysis, the proportions of only the amino acids of Gly, Leu, Phe, Arg., Ile, Asp and Glu were calculated.

$[\alpha]_D^{20}$ determination; C=0.4, 0.01N—HCl TLC.Rf value determination; butanol/acetic acid/pyridine/water=15:5:5:8

The following compounds obtained in the examples ere tested in the same way as described above.

TABLE 9

| | Tail Pinch Method (ED$_{50}$, mg/Kg) | |
|---|---|---|
| | i.v. | s.c. |
| Example 30 | 0.7 | 1.9 |
| 31 | 0.5 | 1.2 |
| 34 | 2.1 | 0.9 |
| 36 | 0.2 | 0.4 |
| 38 | 1.7 | 0.6 |
| Dynorphin (1–13) | >25.0 | |

TABLE 10

| | Rabbit vas deferens Method IC$_{50}$ (nM) |
|---|---|
| Example 30 | 17.8 |
| 31 | 24.5 |
| 36 | 11.2 |
| Dynorphin A (1–17) | 17.4 |

TABLE 11

| Test Compound | Tail Pinch Method ED$_{50}$ (mg/Kg) | Minimum Lethal Dose (mg/Kg) |
|---|---|---|
| Example 30 | 1.9 | >100 |
| Example 31 | 1.2 | >100 |

| Test Compound | Tail Pinch Method ED$_{50}$ (mg/Kg) | Minimum Lethal Dose (mg/Kg) |
|---|---|---|
| Example 36 | 0.4 | >100 |

The embodiments of the invention in which an exclusive property or privilege is claimed are defined as follows:

1. A polypeptide having the formula:

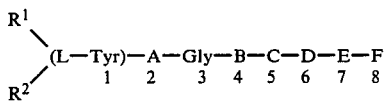

wherein R$^1$ and R$^2$ can be the same or different and each is hydrogen, lower alkyl or lower alkenyl; A is selected from the group consisting of D-Met, D-Ala, D-Ser, D-Cys, D-Thr, Gly and Sar, provided that when A is D-Cys, it is bonded with L-Cys or D-Cys located in position 5 through a S—S bond to effect intramolecular ring closure; B is L-Phe or D-Phe in which the benzene ring can be substituted or an α-N-alkyl derivative thereof; C is selected from the group consisting of L-Leu, L-Ile, L-Nle, L-tert.-Leu, L-Met, L-Met(O), L-Ser, L-Cys, L-Val, D-Cys and α-N-alkyl derivatives thereof, provided that when A is D-Cys, C is L-Cys or D-Cys and C is bonded with A through said S—S bond; D and E each is selected from the group consisting of L-Arg, D-Arg, L-Lys, D-Lys, L-homo-Arg, D-homo-Arg, L-Orn, D-Orn and α-N-alkyl derivatives thereof; F is OR$^3$,

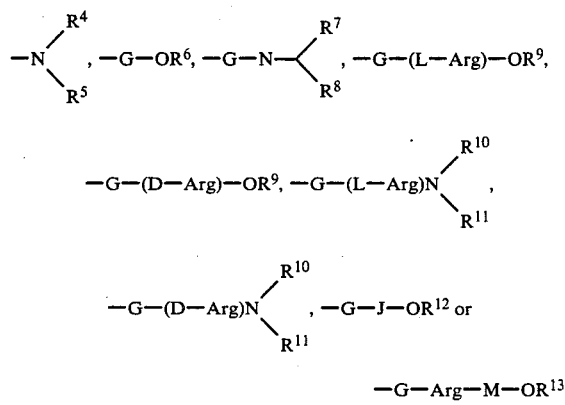

in which R$^3$, R$^4$, R$^5$, R$^6$, R$^7$, R$^8$, R$^9$, R$^{10}$, R$^{11}$, R$^{12}$, and R$^{13}$ are the same or different and each is hydrogen or lower alkyl, G is selected from the group consisting of Gly, Ala, Val, Leu, Ile, Ser, Thr, Cys, Met, Asp, Glu, Asn, Gln, Pro, Lys, Orn, Arg, His, Phe, Tyr, Trp, tert.-Leu, 2-aminoisobutyric acid, α-methyl-Leu, β-alanine, γ-aminobutyric acid and α-N-alkyl derivatives thereof, J is selected from the group consisting of Gly, Sar, L-Ala, D-Ala, L-Phe, D-Phe, L-Asp and D-Asp, and M is selected from the group consisting of D-Pro, D-ala and D-Glu, provided that at least one of A, B, C, D, E and F comprises a D-amino acid or an N-alkyl derivative of a D-amino acid or a L-amino acid, or a pharmacologically acceptable salt of said polypeptide.

2. A polypeptide as claimed in claim 1 having the formula CH$_3$Tyr-Gly-Gly-Phe-Leu-Arg-CH$_3$Arg-(D-Leu)-NHC$_2$H$_5$.

3. A polypeptide as claimed in claim 1 having the formula

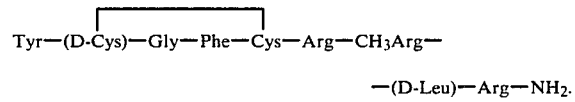

4. A polypeptide as claimed in claim 1 having the formula CH$_3$Tyr-Gly-Gly-Phe-Leu-Arg-CH$_3$Arg-(D-Leu)-NH$_2$.

5. A polypeptide as claimed in claim 1 having the formula

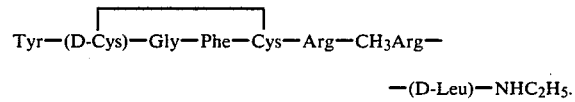

6. A polypeptide as claimed in claim 1 having the formula CH$_3$Tyr-Gly-Gly-Phe-Leu-Arg-CH$_3$Arg-(D-Leu)-Arg-NHC$_2$H$_5$.

7. A polypeptide as claimed in claim 1 having the formula CH$_3$Tyr-Gly-Gly-Phe-Leu-Arg-CH$_3$Arg-(D-Ala)-OH.

8. A polypeptide as claimed in claim 1 having the formula CH$_3$Tyr-Gly-Gly-Phe-Leu-Arg-CH$_3$Arg-CH$_3$Ala-OH.

9. A polypeptide as claimed in claim 1 having the formula CH$_3$Tyr-Gly-Gly-Phe-Leu-Arg-CH$_3$Arg-CH$_3$Ile-OH.

10. A polypeptide as claimed in claim 1 having the formula CH$_3$Tyr-Gly-Gly-Phe-Leu-Arg-CH$_3$Arg-Aib-OH.

11. A polypeptide as claimed in claim 1 having the formula CH$_3$Tyr-Gly-Gly-Phe-Leu-Arg-CH$_3$Arg-(D-Leu)-Sar-OH.

12. A polypeptide as claimed in claim 1 having the formula

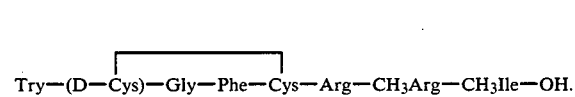

13. A polypeptide as claimed in claim 1 in which the sequence

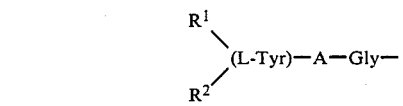

is CH$_3$Tyr-Gly-Gly.

14. A polypeptide as claimed in claim 1 in which the sequence -B-C-D-E- is -Phe-Leu-Arg-CH$_3$Arg-.

15. A polypeptide as claimed in claim 1 in which the sequence

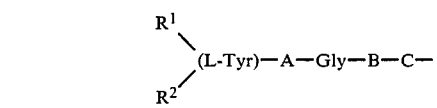

-continued is Tyr—(D-Cys)—Gly—Phe—Cys—.

16. A polypeptide as claimed in claim 1 in which the sequence

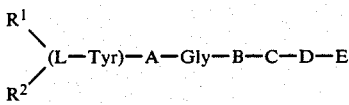

is CH₃Tyr-Gly-Gly-Phe-Leu-Arg-CH₃Arg-.

17. The polypeptide of claim 1 where A is selected from the group consisting of Gly and Sar.

18. The polypeptide of claim 1 where the benzene ring of B is substituted with a member selected from the group consisting of a nitro group, halogen atoms, CF₃, lower alkyl groups and lower alkoxy groups.

19. The polypeptide of claim 1 where C is selected from the group consisting of L-Leu, L-Ile, L-Nle, L-tert.-Leu, L-Met(O), L-Ser, L-Cys, L-Val, D-Cys and α-N-alkyl derivatives thereof, 20. The polypeptide of claim 1 where G is selected from the group consisting of L-Ile, L-Leu, L-Ala, L-Val, L-Asp, L-Pro, L-tert.-Leu, D-Ala, D-Val, D-Leu, D-Pro, 2-aminoisobutyric acid and α-methyl-Leu.

21. The polypeptide of claim 1 wherein F is OR³ or

22. The polypeptide of claim 1 wherein F is

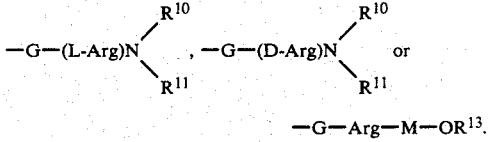

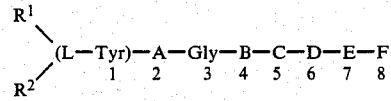

23. An analgesic composition comprising, as an active ingredient, a therapeutically effective amount of a polypeptide of the formula:

$$\begin{matrix} R^1 \\ \phantom{R^1}\diagdown \\ \phantom{R^1R^2}(L\text{-Tyr})\text{—}A\text{—Gly—}B\text{—}C\text{—}D\text{—}E\text{—}F \\ R^2\diagup \phantom{XXXXX} 1\ \ 2\ \ \ \ 3\ \ \ 4\ \ 5\ \ 6\ \ 7\ \ 8 \end{matrix}$$

wherein R¹ and R² can be the same or different and each is hydrogen, lower alkyl or lower alkenyl; A is selected from the group consisting of D-Met, D-Ala, D-Ser, D-Cys, D-Thr, Gly and Sar, provided that when A is D-Cys, it is bonded with L-Cys or D-Cys located in position 5 through a S—S bond to effect intramolecular ring closure; B is L-Phe or D-Phe in which the benzene ring can be substituted or an α-N-alkyl derivative thereof; C is selected from the group consisting of L-Leu, L-Ile, L-Nle, L-tert.-Leu, L-Met, L-Met(O), L-Ser, L-Cys, L-Val, D-Cys and α-N-alkyl derivatives thereof, provided that when A is D-Cys, C is L-Cys or D-Cys and C is bonded with A through said S—S bond; D and E each is selected from the group consisting of L-Arg, D-Arg, L-Lys, D-Lys, L-homo-Arg, D-homo-Arg, L-Orn, D-Orn and α-N-alkyl derivatives thereof; F

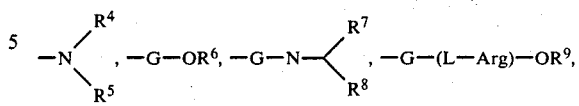

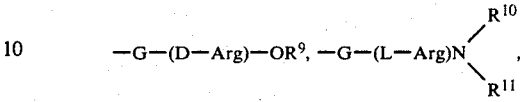

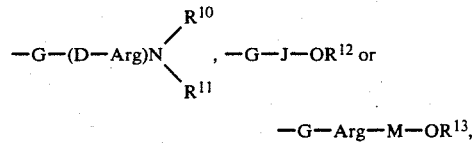

—G—Arg—M—OR¹³, in which R³, R⁴, R⁵, R⁶, R⁷, R⁸, R⁹, R¹⁰, R¹¹, R¹² and R¹³ are the same or different and each is hydrogen or lower alkyl, G is selected from the group consisting of Gly, Ala, Val, Leu, Ile, Ser, Thr, Cys, Met, Asp, Glu, Asn, Gln, Pro, Lys, Orn, Arg, His, Phe, Tyr, Trp, tert.-Leu, 2-aminoisobutyric acid, α-methyl-Leu, β-alanine, γ-aminobutyric acid and α-N-alkyl derivatives thereof, J is selected from the group consisting of Gly, Sar, L-Ala, D-Ala, L-Phe, D-Phe, L-Asp and D-Asp, and M is selected from the group consisting of D-Pro, D-Ala and D-Glu, provided that at least one of A, B, C, D, E and F comprises a D-amino acid or an N-alkyl derivative of a D-amino acid or a L-amino acid, or a pharmacologically acceptable salt of said polypeptide, in combination with a pharmacologically acceptable vehicle.

24. The analgesic composition of claim 23 where A is selected from the group consisting of Gly and Sar.

25. The analgesic composition of claim 23 where the benzene ring of B is substituted with a member selected from the group consisting of a nitro group, halogen atoms, CF₃, lower alkyl groups and lower alkoxy groups, 26. The analgesic composition of claim 23 where C is selected from the group consisting of L-Leu, L-Ile, L-Nle, L-tert.-Leu, L-Met(O), L-Ser, L-Cys, L-Val, D-Cys and α-N-alkyl derivatives thereof.

27. The analgesic composition of claim 23 where G is selected front the group consisting of L-Ile, L-Leu, L-Ala, L-Val, L-Asp, L-Pro, L-tert.-Leu, D-Ala, D-Val, D-Leu, D-Pro, 2-aminoisobutyric acid and α-methyl-Leu.

28. The analgesic composition of claim 23 wherein F is OR³ or

29. the analgesic composition of claim 23 wherein F is

—G—(L-Arg)—OR⁹, —G—(D-Arg)—OR⁹,

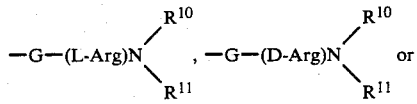

—G—Arg—M—OR¹³.

* * * * *

UNITED STATES PATENT AND TRADEMARK OFFICE
CERTIFICATE OF CORRECTION

PATENT NO. : 4 707 468

DATED : November 17, 1987

INVENTOR(S) : Hiroshi YOSHINO et al

It is certified that error appears in the above-identified patent and that said Letters Patent is hereby corrected as shown below:

Column 46, line 2; after "F" insert ---is $OR^3$,---.

line 45; change "front" to ---from---.

Signed and Sealed this

Thirty-first Day of May, 1988

Attest:

DONALD J. QUIGG

Attesting Officer

Commissioner of Patents and Trademarks